US011097023B1

(12) United States Patent
Bodkhe et al.

(10) Patent No.: US 11,097,023 B1
(45) Date of Patent: Aug. 24, 2021

(54) PRE-FILLED SYRINGE CONTAINING SUGAMMADEX

(71) Applicant: Par Pharmaceutical, Inc., Chestnut Ridge, NY (US)

(72) Inventors: Atul Arvind Bodkhe, Thane (IN); Satish Shamlal Patil, Thane (IN); Jatin Jagdish Gajjar, Thane (IN)

(73) Assignee: Par Pharmaceutical, Inc., Chestnut Ridge, NY (US)

( * ) Notice: Subject to any disclaimer, the term of this patent is extended or adjusted under 35 U.S.C. 154(b) by 0 days.

(21) Appl. No.: 16/919,790

(22) Filed: Jul. 2, 2020

(51) Int. Cl.
*A61K 31/724* (2006.01)
*A61L 2/00* (2006.01)

(52) U.S. Cl.
CPC .......... *A61L 2/0023* (2013.01); *A61K 31/724* (2013.01); *A61L 2202/21* (2013.01); *A61L 2202/23* (2013.01)

(58) Field of Classification Search
CPC ............... A61L 2/0023; A61L 2202/21; A61L 2202/23; A61K 31/724
See application file for complete search history.

(56) References Cited

U.S. PATENT DOCUMENTS

| | | |
|---|---|---|
| 5,332,582 A | 7/1994 | Babcock et al. |
| 5,538,721 A | 7/1996 | Babcock et al. |
| 5,834,446 A | 11/1998 | Dow et al. |
| 6,670,340 B1 | 12/2003 | Zhang et al. |
| 6,949,527 B2 | 9/2005 | Zhang et al. |
| 7,026,304 B2 | 4/2006 | Zhang et al. |
| 7,265,099 B1 | 9/2007 | Born et al. |
| RE44,733 E | 1/2014 | Zhang et al. |
| 9,120,876 B2 | 9/2015 | Davuluri et al. |
| 9,815,911 B2 | 11/2017 | Phanopoulos et al. |
| 9,879,096 B2 | 1/2018 | Ravi et al. |
| 10,017,584 B2 | 7/2018 | Qi |
| 10,233,263 B1 | 3/2019 | Liu et al. |
| 10,336,835 B2 | 7/2019 | Liu et al. |
| 10,385,142 B2 | 8/2019 | Lee et al. |
| 10,414,829 B2 | 9/2019 | Cabri et al. |
| 10,414,830 B2 | 9/2019 | Cabri et al. |
| 10,494,450 B2 | 12/2019 | Alaparthi et al. |
| 10,526,422 B2 | 1/2020 | Jia et al. |
| 2003/0093157 A1* | 5/2003 | Casares ................... A61L 27/48 623/23.73 |
| 2007/0249522 A1* | 10/2007 | Shirley ................... A61K 38/30 514/8.6 |
| 2007/0299035 A1 | 12/2007 | Born et al. |
| 2009/0069412 A1 | 3/2009 | Czarnik |
| 2010/0075938 A1 | 3/2010 | Born et al. |
| 2015/0258279 A1* | 9/2015 | Foster ................... A61K 31/197 604/189 |
| 2018/0016359 A1 | 1/2018 | Jia et al. |
| 2018/0085392 A1 | 3/2018 | Gaspar et al. |
| 2018/0171033 A1* | 6/2018 | Alaparthi ................ A61P 39/02 |
| 2018/0208683 A1 | 7/2018 | Lee et al. |
| 2018/0251575 A1 | 9/2018 | Jia et al. |
| 2018/0312612 A1 | 11/2018 | Lee et al. |
| 2018/0346608 A1 | 12/2018 | Cabri et al. |
| 2018/0355070 A1 | 12/2018 | Cabri et al. |
| 2019/0010255 A1 | 1/2019 | Qi |
| 2019/0062460 A1 | 2/2019 | Liu et al. |
| 2019/0185589 A1 | 6/2019 | Overeem |
| 2019/0284308 A1 | 9/2019 | Cabri et al. |
| 2020/0171244 A1* | 6/2020 | Weikart ................. B65D 23/02 |
| 2020/0237695 A1* | 7/2020 | Chanana ................. A61K 47/12 |

FOREIGN PATENT DOCUMENTS

| | | |
|---|---|---|
| EP | 0447171 A1 | 9/1991 |
| IN | 234112 B | 5/2009 |
| IN | 290882 B | 3/2013 |
| IN | 300063 B | 9/2014 |
| IN | 201409973 P1 | 8/2015 |
| IN | 201727007741 A | 5/2017 |
| IN | 201741012475 A | 10/2018 |
| IN | 201917001361 A | 3/2019 |
| IN | 201741037741 A | 4/2019 |
| IN | 201721043157 A | 7/2019 |
| IN | 201927002840 A | 7/2019 |
| IN | 201811011602 A | 10/2019 |
| IN | 201821016359 A | 11/2019 |

(Continued)

OTHER PUBLICATIONS

Messa, A. F., et al in European Journal of Clinical Pharmacy, vol. 19, #5, p. 2, 2017.*
Drzymalski, D. M., et al in Anesthesiology, Nov. 2019, vol. 131, pp. 1036-1045.*
Akiike et al., "Coupled Cyclodextrin Appending Imidazole as an Enzyme Model", Chemistry Letters, The Chemical Society of Japan, pp. 1089-1092, 1994.
Baer et al., "Heptakis[6-S(2,3-dihydroxypropyl) -6-thio] cyclomaltoheptaose and its sulfone: water-soluble B-cyclodextrin derivatives having modified polarity" Carbohydrate Research 280 (1996), pp. 315-321.

(Continued)

*Primary Examiner* — Gollamudi S Kishore
(74) *Attorney, Agent, or Firm* — Arent Fox LLP

(57) ABSTRACT

A method for providing a sterile pharmaceutical composition in a pre-filled syringe, the method including solubilizing an active agent and a pH adjusting agent in a solvent to provide a pharmaceutical composition, filtering the pharmaceutical composition through a membrane to provide a sterile pharmaceutical composition, and providing the sterile pharmaceutical composition in a pre-filled syringe having a labeled size, wherein the active agent includes sugammadex, the pre-filled syringe has a headspace volume that is less than 7.5% of the labeled size, and the method is free of a heat-based sterilization process. Also provided are sterile pharmaceutical compositions prepared according to the method.

8 Claims, 1 Drawing Sheet

(56) References Cited

FOREIGN PATENT DOCUMENTS

| WO | 2008065142 A1 | 6/2008 |
|---|---|---|
| WO | 2016194001 A1 | 12/2016 |
| WO | 2017084401 A1 | 5/2017 |
| WO | 2017144734 A2 | 8/2017 |
| WO | 2017163165 A1 | 9/2017 |
| WO | 2018036353 A1 | 3/2018 |
| WO | 2018185784 A1 | 10/2018 |

OTHER PUBLICATIONS

Fujita et al., "Selectivity Variation in Hydrolysis of Phenyl Acetates by Simple Modifications of B-Cyclodextrin" Tetrahedron Letters. vol. 21, No. 16, 1980, pp. 1541-1544.

Guillo et al., "Synthesis of symmetrical cyclodetrin derivatives bearing multiple charges" Bulletin De La Societe Chimique De France, 1995, 132, pp. 857-866.

Kuroda et al., "Dynamic Molecular Motions of p-Methylcinnamic Acid Included into B-Cyclodextrin Derivatives: A New Type of Free-energy Relationship in Complex Formation" Journal of the Chemical Society, Perkin Transactions II, 1989, pp. 1355-1592.

Ling et al., "6-S-Hydroxyethylated 6-Thiocyclodextrins: Expandable Host Molecules" Journal of the Chemical Society, Chemical Communications, No. 2, 1993, pp. 203-205.

Tabushi et al., "Artificial Receptors for Amino Acids in Water. Local Environmental Effect of Polar Recognition by 6A-Amino-6B-carboxy- and 6B-Amino-6A-carboxy-B-cyclodextrins" Journal of the American Society, vol. 108, No. 15, 1986, pp. 4514-4518.

Prescribing Information for BRIDION (sugammadex) Injection, Merck & Co., Inc., pp. 1-20.

\* cited by examiner

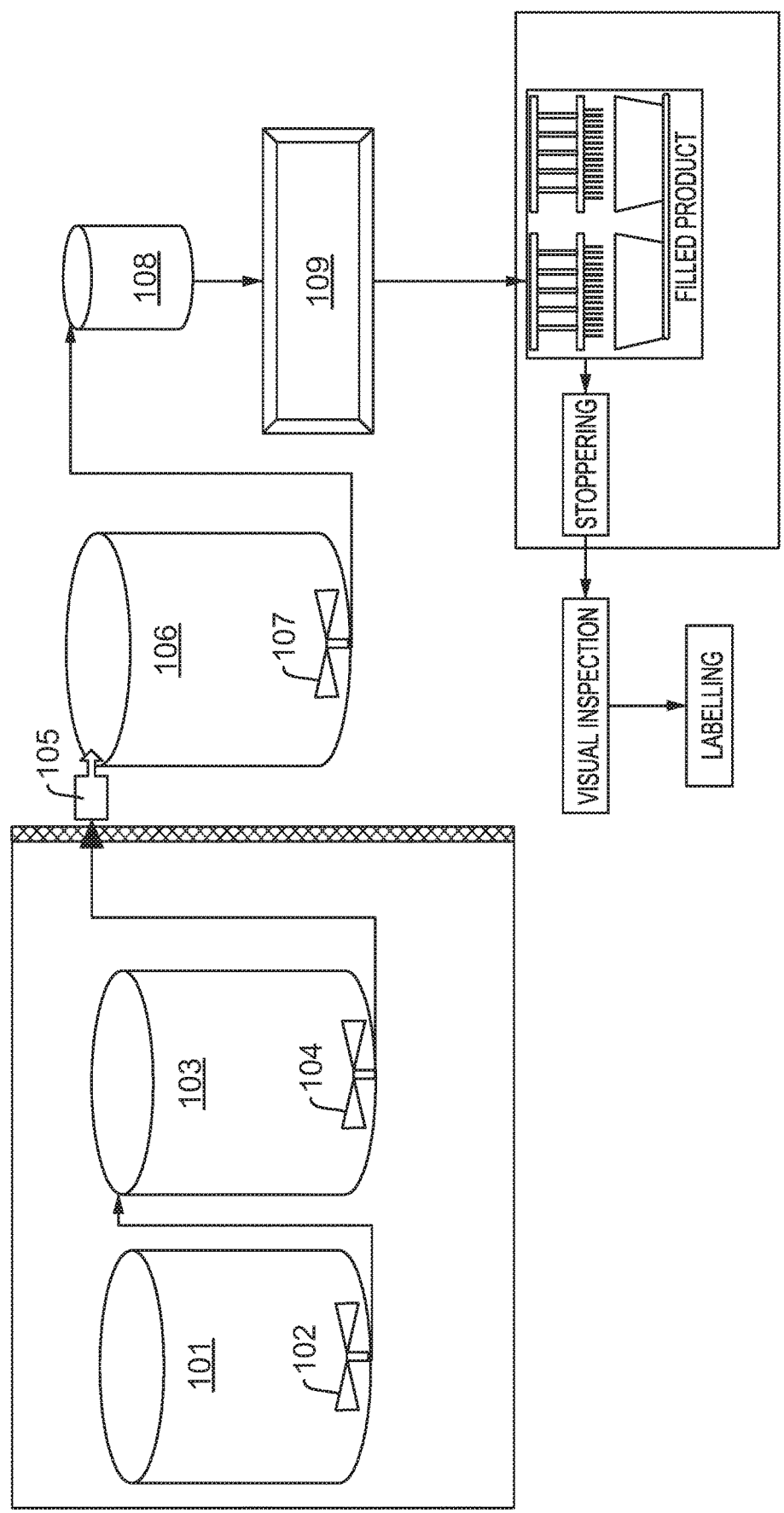

US 11,097,023 B1

PRE-FILLED SYRINGE CONTAINING SUGAMMADEX

TECHNICAL FIELD

The present disclosure is directed to pre-filled syringes containing sugammadex and methods of making the same.

BACKGROUND

Sugammadex sodium (tradename BRIDION®) is a selective relaxant binding agent (SRBA) commonly used for the reversal of neuromuscular blockade induced in general anesthesia. BRIDION® is presented as an aqueous solution contained in a 2 mL or 5 mL glass vial having a specified overfill capacity as required by USP <1151> Pharmaceutical Dosage Forms. Current methods for producing BRIDION® include a terminal sterilization process wherein the aqueous product is subjected to high temperatures (normally 121° C.) in steam sterilizer.

Several insufficiencies exist with current sugammadex sodium-containing products. For example, the overfill capacity required for 2 mL and 5 mL glass vials provides for the generation of oxidative impurities resulting from the reaction of sugammadex sodium with oxygen in the headspace gas. Further, an attempt to minimize oxygen in the headspace of glass vials by, for example, flushing the vials with an inert gas or by the application of vacuum demands special arrangements in manufacturing lines involving additional capital investments, qualifications, training, and aseptic interventions. In addition, in order to ensure 100% replacement of headspace oxygen in each vial, an additional in-process check would be required for headspace analysis using a headspace analyzer, which involves additional investments and expenses for integration with the filling lines. These special requirements increase the manufacturing overhead cost and ultimately increase the cost of the medication. Further, exposure of a glass container to sugammadex sodium during a terminal sterilization process may result in glass delamination, as set forth in USP <1660>.

There is thus a need in the art for an improved method for providing a sterile pharmaceutical composition comprising sugammadex having an acceptable initial impurity level and an acceptable impurity level throughout shelf life.

SUMMARY

The present disclosure is directed to a method for providing a sterile pharmaceutical composition, and in particular, a sterile pharmaceutical composition comprising sugammadex. The method may comprise a preparation step, a filtration step, and a containment step. According to some aspects, one or more of the steps may be performed at a temperature sufficient to provide an acceptable shelf life as described herein.

The present disclosure is also directed to sterile pharmaceutical compositions provided by the method described herein. According to some aspects, the sterile pharmaceutical composition comprises sugammadex as an active agent and is provided in a pre-filled syringe having an acceptable headspace. The sterile pharmaceutical composition may have an acceptable initial impurity level and an acceptable impurity level after a certain period of shelf life. The sterile pharmaceutical composition may be useful for reversing neuromuscular blockade, particularly for reversing neuromuscular blockade after the intraoperative use of a neuromuscular blocking agent such as rocuronium bromide and vecuronium bromide.

BRIEF DESCRIPTION OF THE DRAWING

FIG. 1 shows an example schematic of a method according to the present disclosure.

DETAILED DESCRIPTION

The present disclosure is directed to a method for providing a sterile pharmaceutical composition, and in particular, a sterile pharmaceutical composition comprising sugammadex. The method may comprise a preparation step, a filtration step, and a containment step. According to some aspects, one or more of the steps may be performed at a temperature sufficient to provide an acceptable shelf life as described herein.

The present disclosure is also directed to sterile pharmaceutical compositions provided by the method as described herein. According to some aspects, the sterile pharmaceutical composition comprises sugammadex as an active agent and is provided in a pre-filled syringe having an acceptable headspace. The sterile pharmaceutical composition may have an acceptable initial impurity level and an acceptable impurity level after a certain period of shelf life. The sterile pharmaceutical composition may be useful for reversing neuromuscular blockade, particularly for reversing neuromuscular blockade after the intraoperative use of a neuromuscular blocking agent such as rocuronium bromide and vecuronium bromide.

According to some aspects, the pharmaceutical composition comprises an active agent, at least one pH adjusting agent, and a solvent. The active agent may comprise sugammadex. In some examples, at least a portion of the active agent may be provided as a salt. Examples of active agent salts include, but are not limited to, acetate, carbonate, citrate, hydrochloride, hydrocyanide, hydrofluoride, nitrate, nitrite, phosphate, sulfate, and sodium salts. In one example, the active agent may be provided as sugammadex sodium.

According to some aspects, the pharmaceutical composition may have a concentration of active agent sufficient for any of the uses described herein, and in particular, for reversing neuromuscular blockade after administration of a neuromuscular blocking agent. For example, the pharmaceutical composition may have a concentration of sugammadex of between about 1 and 500 mg/mL, optionally between about 1 and 250 mg/mL, optionally between about 50 and 150 mg/mL, and optionally about 100 mg/mL. It should be understood that if the active agent or a portion thereof is provided as a salt, the concentration of active agent salt may be higher than the concentration of active agent. For example, a pharmaceutical composition comprising sugammadex at a concentration of about 100 mg/mL may comprise sugammadex sodium at a concentration of about 108.8 mg/mL. It should be understood that the concentration of active agent salt may be selected to provide the active agent concentration as described herein.

According to some aspects, the pharmaceutical composition comprises a pH adjusting agent. As used herein, the term "pH adjusting agent" refers to a component or combination of components sufficient to adjust a pharmaceutical composition's pH. According to some aspects, the pH adjusting agent is sufficient to raise or lower the pharmaceutical composition's initial pH to a pharmaceutically acceptable range (i.e., not toxic or producing unacceptable side effects). Additionally or alternatively, the pH adjusting agent may be sufficient to maintain the pharmaceutical composition's pH in a pharmaceutically acceptable range over a certain period of shelf life. According to some aspects, the pharmaceutically acceptable pH range may be between about 6 and 9, optionally between about 6.5 and 8.5, optionally between about 7 and 8, optionally between about 7.5 and 8.5, and optionally from more than 8.0 to 8.5. According to some aspects, the pharmaceutically acceptable pH range may be more than 8.0.

According to some aspects, the one or more pH adjusting agents may comprise acetic acid, adipic acid, ascorbic acid, citric acid, hydrochloric acid, lactic acid, malic acid, monopotassium phosphate, monosodium phosphate, phosphoric acid, pyrophosphoric acid, succinic acid, sulfuric acid, tartaric acid, lithium hydroxide, sodium hydroxide, potassium hydroxide, rubidium hydroxide, cesium hydroxide, calcium hydroxide, strontium hydroxide, barium hydroxide, or a combination thereof. In one example, the pharmaceutical composition comprises hydrochloric acid, sodium hydroxide, or a combination thereof.

According to some aspects, each of the pH adjusting agents may together or independently have a concentration of from about 0.001 N to about 10 N, optionally from about 0.01 N to about 1 N.

According to some aspects, the sterile pharmaceutical composition may be free of pH adjusting agents as described herein. It should be understood that the pH-adjusting agent-free sterile pharmaceutical composition may have an initial pH within a pharmaceutically acceptable pH range, as described herein and/or may have a pH in a pharmaceutically acceptable range over a certain period of shelf life, as described herein.

According to some aspects, the solvent may be acceptable for pharmaceutical administration. Examples of methods of pharmaceutical administration include, but are not limited to, subcutaneous, intracameral, intravenous, and intramuscular injection, infusion, intra-arterial administration, intra-cardiac injection, endotracheal administration, intraosseous administration, oral inhalation, topical administration, and as ophthalmic irrigation.

According to some aspects, the solvent may comprise one or more of acetic acid, acetone, acetonitrile, animal oil, aqueous buffer, benzene, bisabolol, butanol, carbon tetrachloride, chlorobenzene, chloroform, dimethylformamide, dioxane, essential oil, ethanol, ethyl acetate, ethyl oleate, ethylene chloride, fatty acid esters, glycerin, glycofurol, hexane, hydrogenated vegetable oil, isopropanol, isopropyl alcohol, isopropyl myristate, isopropyl palmitate, methanol, methylene chloride, mineral oil, polyethylene glycol, polyol, propylene glycol, silicone fluid glyceride, squalane, terpene, tetrahydrofuran, toluene, triacetin, tributyl citrate, triethyl citrate, vegetable oil, and water. In one example, the solvent comprises water for injection (WFI). As used herein, the term "water for injection" or "WFI" refers to sterile, non-pyrogenic, distilled water suitable for intravenous administration after addition of a suitable solute. According to some aspects, WFI may refer to water that meets USP requirements for WFI. For example, WFI may refer to water that comprises less than 0.25 USP Endotoxin Unit/mL per the Bacterial Endotoxins Test <85>, meets the requirements as set forth in Water Conductivity, Bulk Water <645>, and meets the requirements as set forth in Total Organic Carbon <643>.

According to some aspects, the pharmaceutical composition may have an osmolality of between about 100 and 700 mosmol/kg, optionally between about 200 and 600 mosmol/kg, and optionally between about 200 and 500 mosmol/kg.

According to some aspects, the sterile pharmaceutical composition may comprise one or more processing aids. As used herein, the term "processing aid" refers to a pharmaceutical composition component resulting from one or more processing steps, particularly one or more of the processing steps as described herein. Example processing aids according to the present disclosure include, but are not limited to, components of a headspace as will be described herein, such as nitrogen, carbon dioxide, or a combination thereof.

According to some aspects, the sterile pharmaceutical composition may have a formulation consisting of 100 mg/mL of sugammadex provided as sugammadex sodium, water for injection, and a q.s. concentration of nitrogen. According to some aspects, the sterile pharmaceutical composition may have a formulation consisting of 100 mg/mL of sugammadex provided as sugammadex sodium, water for injection, and a q.s. concentration of carbon dioxide.

The pharmaceutical composition according to the present disclosure may have an acceptable initial impurity level and an acceptable impurity level after a certain period of shelf life. As used herein, the term "impurity" refers to an undesired substance in a composition. It should be understood that one or more impurities may be present in an initial composition and/or may be formed after a certain period of shelf life of a composition. For example, one or more impurities may be formed via degradation of one or more components of the composition, such as the active agent. Sources of degradation include, but are not limited to, oxidation, racemization, visible light, ultraviolet light, moisture, heat (including heat from a sterilization process), changes in pH, and composition component interactions.

Example impurities according to the present disclosure include, but are not limited to, sugammadex s-oxide diastereomer—1 impurity, sugammadex s-oxide diastereomer—2 impurity, sugammadex mono chloro impurity, and sugammadex mono hydroxyl impurity. Other example impurities according to the present disclosure include, but are not limited to, monohydroxy sugammadex sodium, sugammadex dihydroxy impurity, mono halogen sugammadex chloride, monothio sugammadex sodium, mono thio mono hydroxy sugammadex, mono sulfoxide sugammadex, sugammadex sulfone sodium salt, sugammadex methyl ester, γ-cyclodextrin, sugammadex disulfide impurity, sugammadex mono bromo impurity, 2-hydroxypropyl-β-cyclodextrin, alpha cyclodextrin, beta cyclodextrin, gamma cyclodextrin, 3-((3-mercaptopropanoyl)thio)propanoic acid, sugammadex disulfide sodium salt, monobromo sugammadex sodium, triacetyl-β-cyclodextrin, sugammadex tppo analogue, sugammadex n,n-dimethyl impurity, sugammadex n,n-dimethyl impurity, sugammadex thiolactic acid impurity, sugammadex dehydro-impurity, mono-sulfoxide-sugammadex epimer I, mono-sulfoxide-sugammadex epimer II, sugammadex monothioglycolic acid impurity, sugammadex ether impurity, sugammadex monothiol impurity, sugammadex di-sulfoxide impurity, diphenyl phosphine oxide impurity, sugammadex impurity 47, sugammadex impurity 25, and sugammadex disulfide dimer.

According to some aspects, the impurities according to the present disclosure may include unknown impurities generated upon sugammadex thermal degradation and/or upon sugammadex oxidation.

According to some aspects, the unknown impurities may comprise at least one substance that is not sugammadex s-oxide diastereomer—1 impurity, sugammadex s-oxide diastereomer—2 impurity, sugammadex mono chloro impurity, or sugammadex mono hydroxyl impurity, and is present in a sugammadex sodium-containing composition having an initial sugammadex concentration of 100 mg/mL in WFI after the composition has been subjected to thermal forced degradation conditions, wherein thermal forced degradation conditions are a temperature of about 60° C. and a relative humidity of about 60% RH for a time period of at least one day, optionally for a time period of ten days.

Additionally or alternatively, the unknown impurities may comprise at least one substance that is not sugammadex s-oxide diastereomer—1 impurity, sugammadex s-oxide diastereomer—2 impurity, sugammadex mono chloro impurity, or sugammadex mono hydroxyl impurity, and is present in a sugammadex sodium-containing composition having an initial sugammadex concentration of 100 mg/mL in WFI after the composition has been subjected to oxidative forced degradation conditions, wherein oxidative forced degradation conditions are an atmosphere containing 0.01% $H_2O_2$ for a time period of at least one hour, or an atmosphere containing 0.002% $H_2O_2$ for a time period of at least one hour, optionally for a time period of five hours.

According to some aspects, the pharmaceutical composition may have an initial total impurity concentration of no more than about 5%, more preferably no more than about 4.5%, more preferably no more than about 4%, more preferably no more than about 3.5%, more preferably no more than about 3%, more preferably no more than about 2.5%, more preferably no more than about 2%, more preferably no more than about 1.5%, more preferably no more than about 1%, and most preferably no more than about 0.5%. Unless indicated otherwise, the percentages of impurities expressed herein are expressed as % (w/w) of the active agent.

According to some aspects, the pharmaceutical composition may have an initial total impurity concentration of no more than about 1%, more preferably no more than about 0.99%, more preferably no more than about 0.98%, more preferably no more than about 0.97%, more preferably no more than about 0.96%, more preferably no more than about 0.95%, more preferably no more than about 0.94%, more preferably no more than about 0.93%, more preferably no more than about 0.92%, more preferably no more than about 0.91%, more preferably no more than about 0.90%, more preferably no more than about 0.89%, more preferably no more than about 0.88%, more preferably no more than about 0.87%, more preferably no more than about 0.86%, more preferably no more than about 0.85%, more preferably no more than about 0.84%, more preferably no more than about 0.83%, more preferably no more than about 0.82%, more preferably no more than about 0.81%, more preferably no more than about 0.80%, more preferably no more than about 0.79%, more preferably no more than about 0.78%, more preferably no more than about 0.77%, more preferably no more than about 0.76%, more preferably no more than about 0.75%, more preferably no more than about 0.74%, more preferably no more than about 0.73%, more preferably no more than about 0.72%, more preferably no more than about 0.71%, more preferably no more than about 0.97%, more preferably no more than about 0.69%, more preferably no more than about 0.68%, more preferably no more than about 0.67%, more preferably no more than about 0.66%, more preferably no more than about 0.65%, more preferably no more than about 0.64%, more preferably no more than about 0.63%, more preferably no more than about 0.62%, more preferably no more than about 0.61%, more preferably no more than about 0.60%, more preferably no more than about 0.59%, more preferably no more than about 0.58%, more preferably no more than about 0.57%, more preferably no more than about 0.56%, more preferably no more than about 0.55%, more preferably no more than about 0.54%, more preferably no more than about 0.53%, more preferably no more than about 0.52%, more preferably no more than about 0.51%, more preferably no more than about 0.50%, more preferably no more than about 0.49%, more preferably no more than about 0.48%, more preferably no more than about 0.47%, more preferably no more than about 0.46%, more preferably no more than about 0.45%, more preferably no more than about 0.44%, more preferably no more than about 0.43%, more preferably no more than about 0.42%, more preferably no more than about 0.41%, more preferably no more than about 0.40%, more preferably no more than about 0.39%, more preferably no more than about 0.38%, more preferably no more than about 0.37%, more preferably no more than about 0.36%, more preferably no more than about 0.35%, more preferably no more than about 0.34%, more preferably no more than about 0.33%, more preferably no more than about 0.32%, more preferably no more than about 0.31%, more preferably no more than about 0.30%, more preferably no more than about 0.29%, more preferably no more than about 0.28%, more preferably no more than about 0.27%, more preferably no more than about 0.26%, more preferably no more than about 0.25%, more preferably no more than about 0.24%, more preferably no more than about 0.23%, more preferably no more than about 0.22%, more preferably no more than about 0.21%, more preferably no more than about 0.20%, more preferably no more than about 0.19%, more preferably no more than about 0.18%, more preferably no more than about 0.17%, more preferably no more than about 0.16%, more preferably no more than about 0.15%, more preferably no more than about 0.14%, more preferably no more than about 0.13%, more preferably no more than about 0.12%, more preferably no more than about 0.11%, more preferably no more than about 0.10%, more preferably no more than about 0.09%, more preferably no more than about 0.08%, more preferably no more than about 0.07%, more preferably no more than about 0.06%, more preferably no more than about 0.05%, more preferably no more than about 0.04%, more preferably no more than about 0.03%, more preferably no more than about 0.02%, and most preferably no more than about 0.01%.

According to some aspects, the pharmaceutical composition may have a total impurity concentration after a certain period of shelf life of no more than about 5%, more preferably no more than about 4.5%, more preferably no more than about 4%, more preferably no more than about 3.5%, more preferably no more than about 3%, more preferably no more than about 2.5%, more preferably no more than about 2%, more preferably no more than about 1.5%, more preferably no more than about 1%, and most preferably no more than about 0.5%.

According to some aspects, the pharmaceutical composition may have a total impurity concentration after a certain period of shelf life of no more than about 1%, more preferably no more than about 0.99%, more preferably no more than about 0.98%, more preferably no more than about 0.97%, more preferably no more than about 0.96%, more preferably no more than about 0.95%, more preferably no more than about 0.94%, more preferably no more than about 0.93%, more preferably no more than about 0.92%, more preferably no more than about 0.91%, more preferably no more than about 0.90%, more preferably no more than about 0.89%, more preferably no more than about 0.88%, more preferably no more than about 0.87%, more preferably no more than about 0.86%, more preferably no more than about 0.85%, more preferably no more than about 0.84%, more preferably no more than about 0.83%, more preferably no more than about 0.82%, more preferably no more than about 0.81%, more preferably no more than about 0.80%, more preferably no more than about 0.79%, more preferably no more than about 0.78%, more preferably no more than about 0.77%, more preferably no more than about 0.76%, more preferably no more than about 0.75%, more preferably no more than about 0.74%, more preferably no more than about 0.73%, more preferably no more than about 0.72%, more preferably no more than about 0.71%, more preferably no more than about 0.97%, more preferably no more than about 0.69%, more preferably no more than about 0.68%, more preferably no more than about 0.67%, more preferably no more than about 0.66%, more preferably no more than about 0.65%, more preferably no more than about 0.64%, more preferably no more than about 0.63%, more preferably no more than about 0.62%, more preferably no more than about 0.61%, more preferably no more than about 0.60%, more preferably no more than about 0.59%, more preferably no more than about 0.58%, more preferably no more than about 0.57%, more preferably no more than about 0.56%, more preferably no more than about 0.55%, more preferably no more than about 0.54%, more preferably no more than about 0.53%, more preferably no more than about 0.52%, more preferably no more than about 0.51%, more preferably no more than about 0.50%, more preferably no more than about 0.49%, more preferably no more than about 0.48%, more preferably no more than about 0.47%, more preferably no more than about 0.46%, more preferably no more than about 0.45%, more preferably no more than about 0.44%, more preferably no more than about 0.43%, more preferably no more than about 0.42%, more preferably no more than about 0.41%, more preferably no more than about 0.40%, more preferably no more than about 0.39%, more preferably no more than about 0.38%, more preferably no more than about 0.37%, more preferably no more than about 0.36%, more preferably no more than about 0.35%, more preferably no more than about 0.34%, more preferably no more than about 0.33%, more preferably no more than about 0.32%, more preferably no more than about 0.31%, more preferably no more than about 0.30%, more preferably no more than about 0.29%, more preferably no more than about 0.28%, more preferably no more than about 0.27%, more preferably no more than about 0.26%, more preferably no more than about 0.25%, more preferably no more than about 0.24%, more preferably no more than about 0.23%, more preferably no more than about 0.22%, more preferably no more than about 0.21%, more preferably no more than about 0.20%, more preferably no more than about 0.19%, more preferably no more than about 0.18%, more preferably no more than about 0.17%, more preferably no more than about 0.16%, more preferably no more than about 0.15%, more preferably no more than about 0.14%, more preferably no more than about 0.13%, more preferably no more than about 0.12%, more preferably no more than about 0.11%, more preferably no more than about 0.10%, more preferably no more than about 0.09%, more preferably no more than about 0.08%, more preferably no more than about 0.07%, more preferably no more than about 0.06%, more preferably no more than about 0.05%, more preferably no more than about 0.04%, more preferably no more than about 0.03%, more preferably no more than about 0.02%, and most preferably no more than about 0.01%.

According to some aspects, the pharmaceutical composition may have an initial sugammadex s-oxide diastereomer—1 impurity concentration of no more than about 5%, more preferably no more than about 4.5%, more preferably no more than about 4%, more preferably no more than about 3.5%, more preferably no more than about 3%, more preferably no more than about 2.5%, more preferably no more than about 2%, more preferably no more than about 1.5%, more preferably no more than about 1%, and most preferably no more than about 0.5%.

According to some aspects, the pharmaceutical composition may have an initial sugammadex s-oxide diastereomer—1 impurity concentration of no more than about 1%, more preferably no more than about 0.99%, more preferably no more than about 0.98%, more preferably no more than about 0.97%, more preferably no more than about 0.96%, more preferably no more than about 0.95%, more preferably no more than about 0.94%, more preferably no more than about 0.93%, more preferably no more than about 0.92%, more preferably no more than about 0.91%, more preferably no more than about 0.90%, more preferably no more than about 0.89%, more preferably no more than about 0.88%, more preferably no more than about 0.87%, more preferably no more than about 0.86%, more preferably no more than about 0.85%, more preferably no more than about 0.84%, more preferably no more than about 0.83%, more preferably no more than about 0.82%, more preferably no more than about 0.81%, more preferably no more than about 0.80%, more preferably no more than about 0.79%, more preferably no more than about 0.78%, more preferably no more than about 0.77%, more preferably no more than about 0.76%, more preferably no more than about 0.75%, more preferably no more than about 0.74%, more preferably no more than about 0.73%, more preferably no more than about 0.72%, more preferably no more than about 0.71%, more preferably no more than about 0.97%, more preferably no more than about 0.69%, more preferably no more than about 0.68%, more preferably no more than about 0.67%, more preferably no more than about 0.66%, more preferably no more than about 0.65%, more preferably no more than about 0.64%, more preferably no more than about 0.63%, more preferably no more than about 0.62%, more preferably no more than about 0.61%, more preferably no more than about 0.60%, more preferably no more than about 0.59%, more preferably no more than about 0.58%, more preferably no more than about 0.57%, more preferably no more than about 0.56%, more preferably no more than about 0.55%, more preferably no more than about 0.54%, more preferably no more than about 0.53%, more preferably no more than about 0.52%, more preferably no more than about 0.51%, more preferably no more than about 0.50%, more preferably no more than about 0.49%, more preferably no more than about 0.48%, more preferably no more than about 0.47%, more preferably no more than about 0.46%, more preferably no more than about 0.45%, more preferably no more than about 0.44%, more preferably no more than about 0.43%, more preferably no more than about 0.42%, more preferably no more than about 0.41%, more preferably no more than about 0.40%, more preferably no more than about 0.39%, more preferably no more than about 0.38%, more preferably no more than about 0.37%, more preferably no more than about 0.36%, more preferably no more than about 0.35%, more preferably no more than about 0.34%, more preferably no more than about 0.33%, more preferably no more than about 0.32%, more preferably no more than about 0.31%, more preferably no more than about 0.30%, more preferably no more than about 0.29%, more preferably no more than about 0.28%, more preferably no more than about 0.27%, more preferably no more than about 0.26%, more preferably no more than about 0.25%, more preferably no more than about 0.24%, more preferably no more than about 0.23%, more preferably no more than about 0.22%, more preferably no more than about 0.21%, more preferably no more than about 0.20%, more preferably no more than about 0.19%, more preferably no more than about 0.18%, more preferably no more than about 0.17%, more preferably no more than about 0.16%, more preferably no more than about 0.15%, more preferably no more than about 0.14%, more preferably no more than about 0.13%, more preferably no more than about 0.12%, more preferably no more than about 0.11%, more preferably no more than about 0.10%, more preferably no more than about 0.09%, more preferably no more than about 0.08%, more preferably no more than about 0.07%, more preferably no more than about 0.06%, more preferably no more than about 0.05%, more preferably no more than about 0.04%, more preferably no more than about 0.03%, more preferably no more than about 0.02%, and most preferably no more than about 0.01%.

According to some aspects, the pharmaceutical composition may have a sugammadex s-oxide diastereomer—1 impurity concentration after a certain period of shelf life of no more than about 5%, more preferably no more than about 4.5%, more preferably no more than about 4%, more preferably no more than about 3.5%, more preferably no more than about 3%, more preferably no more than about 2.5%, more preferably no more than about 2%, more preferably no more than about 1.5%, more preferably no more than about 1%, and most preferably no more than about 0.5%.

According to some aspects, the pharmaceutical composition may have a sugammadex s-oxide diastereomer—1 impurity concentration after a certain period of shelf life of no more than about 1%, more preferably no more than about 0.99%, more preferably no more than about 0.98%, more preferably no more than about 0.97%, more preferably no more than about 0.96%, more preferably no more than about 0.95%, more preferably no more than about 0.94%, more preferably no more than about 0.93%, more preferably no more than about 0.92%, more preferably no more than about 0.91%, more preferably no more than about 0.90%, more preferably no more than about 0.89%, more preferably no more than about 0.88%, more preferably no more than about 0.87%, more preferably no more than about 0.86%, more preferably no more than about 0.85%, more preferably no more than about 0.84%, more preferably no more than about 0.83%, more preferably no more than about 0.82%, more preferably no more than about 0.81%, more preferably no more than about 0.80%, more preferably no more than about 0.79%, more preferably no more than about 0.78%, more preferably no more than about 0.77%, more preferably no more than about 0.76%, more preferably no more than about 0.75%, more preferably no more than about 0.74%, more preferably no more than about 0.73%, more preferably no more than about 0.72%, more preferably no more than about 0.71%, more preferably no more than about 0.97%, more preferably no more than about 0.69%, more preferably no more than about 0.68%, more preferably no more than about 0.67%, more preferably no more than about 0.66%, more preferably no more than about 0.65%, more preferably no more than about 0.64%, more preferably no more than about 0.63%, more preferably no more than about 0.62%, more preferably no more than about 0.61%, more preferably no more than about 0.60%, more preferably no more than about 0.59%, more preferably no more than about 0.58%, more preferably no more than about 0.57%, more preferably no more than about 0.56%, more preferably no more than about 0.55%, more preferably no more than about 0.54%, more preferably no more than about 0.53%, more preferably no more than about 0.52%, more preferably no more than about 0.51%, more preferably no more than about 0.50%, more preferably no more than about 0.49%, more preferably no more than about 0.48%, more preferably no more than about 0.47%, more preferably no more than about 0.46%, more preferably no more than about 0.45%, more preferably no more than about 0.44%, more preferably no more than about 0.43%, more preferably no more than about 0.42%, more preferably no more than about 0.41%, more preferably no more than about 0.40%, more preferably no more than about 0.39%, more preferably no more than about 0.38%, more preferably no more than about 0.37%, more preferably no more than about 0.36%, more preferably no more than about 0.35%, more preferably no more than about 0.34%, more preferably no more than about 0.33%, more preferably no more than about 0.32%, more preferably no more than about 0.31%, more preferably no more than about 0.30%, more preferably no more than about 0.29%, more preferably no more than about 0.28%, more preferably no more than about 0.27%, more preferably no more than about 0.26%, more preferably no more than about 0.25%, more preferably no more than about 0.24%, more preferably no more than about 0.23%, more preferably no more than about 0.22%, more preferably no more than about 0.21%, more preferably no more than about 0.20%, more preferably no more than about 0.19%, more preferably no more than about 0.18%, more preferably no more than about 0.17%, more preferably no more than about 0.16%, more preferably no more than about 0.15%, more preferably no more than about 0.14%, more preferably no more than about 0.13%, more preferably no more than about 0.12%, more preferably no more than about 0.11%, more preferably no more than about 0.10%, more preferably no more than about 0.09%, more preferably no more than about 0.08%, more preferably no more than about 0.07%, more preferably no more than about 0.06%, more preferably no more than about 0.05%, more preferably no more than about 0.04%, more preferably no more than about 0.03%, more preferably no more than about 0.02%, and most preferably no more than about 0.01%.

According to some aspects, the pharmaceutical composition may have an initial sugammadex s-oxide diastereomer—2 impurity concentration of no more than about 5%, more preferably no more than about 4.5%, more preferably no more than about 4%, more preferably no more than about 3.5%, more preferably no more than about 3%, more preferably no more than about 2.5%, more preferably no more than about 2%, more preferably no more than about 1.5%, more preferably no more than about 1%, and most preferably no more than about 0.5%.

According to some aspects, the pharmaceutical composition may have an initial sugammadex s-oxide diastereomer—2 impurity concentration of no more than about 1%, more preferably no more than about 0.99%, more preferably no more than about 0.98%, more preferably no more than about 0.97%, more preferably no more than about 0.96%, more preferably no more than about 0.95%, more preferably no more than about 0.94%, more preferably no more than about 0.93%, more preferably no more than about 0.92%, more preferably no more than about 0.91%, more preferably no more than about 0.90%, more preferably no more than about 0.89%, more preferably no more than about 0.88%, more preferably no more than about 0.87%, more preferably no more than about 0.86%, more preferably no more than about 0.85%, more preferably no more than about 0.84%, more preferably no more than about 0.83%, more preferably no more than about 0.82%, more preferably no more than about 0.81%, more preferably no more than about 0.80%, more preferably no more than about 0.79%, more preferably no more than about 0.78%, more preferably no more than about 0.77%, more preferably no more than about 0.76%, more preferably no more than about 0.75%, more preferably no more than about 0.74%, more preferably no more than about 0.73%, more preferably no more than about 0.72%, more preferably no more than about 0.71%, more preferably no more than about 0.97%, more preferably no more than about 0.69%, more preferably no more than about 0.68%, more preferably no more than about 0.67%, more preferably no more than about 0.66%, more preferably no more than about 0.65%, more preferably no more than about 0.64%, more preferably no more than about 0.63%, more preferably no more than about 0.62%, more preferably no more than about 0.61%, more preferably no more than about 0.60%, more preferably no more than about 0.59%, more preferably no more than about 0.58%, more preferably no more than about 0.57%, more preferably no more than about 0.56%, more preferably no more than about 0.55%, more preferably no more than about 0.54%, more preferably no more than about 0.53%, more preferably no more than about 0.52%, more preferably no more than about 0.51%, more preferably no more than about 0.50%, more preferably no more than about 0.49%, more preferably no more than about 0.48%, more preferably no more than about 0.47%, more preferably no more than about 0.46%, more preferably no more than about 0.45%, more preferably no more than about 0.44%, more preferably no more than about 0.43%, more preferably no more than about 0.42%, more preferably no more than about 0.41%, more preferably no more than about 0.40%, more preferably no more than about 0.39%, more preferably no more than about 0.38%, more preferably no more than about 0.37%, more preferably no more than about 0.36%, more preferably no more than about 0.35%, more preferably no more than about 0.34%, more preferably no more than about 0.33%, more preferably no more than about 0.32%, more preferably no more than about 0.31%, more preferably no more than about 0.30%, more preferably no more than about 0.29%, more preferably no more than about 0.28%, more preferably no more than about 0.27%, more preferably no more than about 0.26%, more preferably no more than about 0.25%, more preferably no more than about 0.24%, more preferably no more than about 0.23%, more preferably no more than about 0.22%, more preferably no more than about 0.21%, more preferably no more than about 0.20%, more preferably no more than about 0.19%, more preferably no more than about 0.18%, more preferably no more than about 0.17%, more preferably no more than about 0.16%, more preferably no more than about 0.15%, more preferably no more than about 0.14%, more preferably no more than about 0.13%, more preferably no more than about 0.12%, more preferably no more than about 0.11%, more preferably no more than about 0.10%, more preferably no more than about 0.09%, more preferably no more than about 0.08%, more preferably no more than about 0.07%, more preferably no more than about 0.06%, more preferably no more than about 0.05%, more preferably no more than about 0.04%, more preferably no more than about 0.03%, more preferably no more than about 0.02%, and most preferably no more than about 0.01%.

According to some aspects, the pharmaceutical composition may have a sugammadex s-oxide diastereomer—2 impurity concentration after a certain period of shelf life of no more than about 5%, more preferably no more than about 4.5%, more preferably no more than about 4%, more preferably no more than about 3.5%, more preferably no more than about 3%, more preferably no more than about 2.5%, more preferably no more than about 2%, more preferably no more than about 1.5%, more preferably no more than about 1%, and most preferably no more than about 0.5%.

According to some aspects, the pharmaceutical composition may have a sugammadex s-oxide diastereomer—2 impurity concentration after a certain period of shelf life of no more than about 1%, more preferably no more than about 0.99%, more preferably no more than about 0.98%, more preferably no more than about 0.97%, more preferably no more than about 0.96%, more preferably no more than about 0.95%, more preferably no more than about 0.94%, more preferably no more than about 0.93%, more preferably no more than about 0.92%, more preferably no more than about 0.91%, more preferably no more than about 0.90%, more preferably no more than about 0.89%, more preferably no more than about 0.88%, more preferably no more than about 0.87%, more preferably no more than about 0.86%, more preferably no more than about 0.85%, more preferably no more than about 0.84%, more preferably no more than about 0.83%, more preferably no more than about 0.82%, more preferably no more than about 0.81%, more preferably no more than about 0.80%, more preferably no more than about 0.79%, more preferably no more than about 0.78%, more preferably no more than about 0.77%, more preferably no more than about 0.76%, more preferably no more than about 0.75%, more preferably no more than about 0.74%, more preferably no more than about 0.73%, more preferably no more than about 0.72%, more preferably no more than about 0.71%, more preferably no more than about 0.97%, more preferably no more than about 0.69%, more preferably no more than about 0.68%, more preferably no more than about 0.67%, more preferably no more than about 0.66%, more preferably no more than about 0.65%, more preferably no more than about 0.64%, more preferably no more than about 0.63%, more preferably no more than about 0.62%, more preferably no more than about 0.61%, more preferably no more than about 0.60%, more preferably no more than about 0.59%, more preferably no more than about 0.58%, more preferably no more than about 0.57%, more preferably no more than about 0.56%, more preferably no more than about 0.55%, more preferably no more than about 0.54%, more preferably no more than about 0.53%, more preferably no more than about 0.52%, more preferably no more than about 0.51%, more preferably no more than about 0.50%, more preferably no more than about 0.49%, more preferably no more than about 0.48%, more preferably no more than about 0.47%, more preferably no more than about 0.46%, more preferably no more than about 0.45%, more preferably no more than about 0.44%, more preferably no more than about 0.43%, more preferably no more than about 0.42%, more preferably no more than about 0.41%, more preferably no more than about 0.40%, more preferably no more than about 0.39%, more preferably no more than about 0.38%, more preferably no more than about 0.37%, more preferably no more than about 0.36%, more preferably no more than about 0.35%, more preferably no more than about 0.34%, more preferably no more than about 0.33%, more preferably no more than about 0.32%, more preferably no more than about 0.31%, more preferably no more than about 0.30%, more preferably no more than about 0.29%, more preferably no more than about 0.28%, more preferably no more than about 0.27%, more preferably no more than about 0.26%, more preferably no more than about 0.25%, more preferably no more than about 0.24%, more preferably no more than about 0.23%, more preferably no more than about 0.22%, more preferably no more than about 0.21%, more preferably no more than about 0.20%, more preferably no more than about 0.19%, more preferably no more than about 0.18%, more preferably no more than about 0.17%, more preferably no more than about 0.16%, more preferably no more than about 0.15%, more preferably no more than about 0.14%, more preferably no more than about 0.13%, more preferably no more than about 0.12%, more preferably no more than about 0.11%, more preferably no more than about 0.10%, more preferably no more than about 0.09%, more preferably no more than about 0.08%, more preferably no more than about 0.07%, more preferably no more than about 0.06%, more preferably no more than about 0.05%, more preferably no more than about 0.04%, more preferably no more than about 0.03%, more preferably no more than about 0.02%, and most preferably no more than about 0.01%.

According to some aspects, the pharmaceutical composition may have an initial sugammadex mono chloro impurity concentration of no more than about 5%, more preferably no more than about 4.5%, more preferably no more than about 4%, more preferably no more than about 3.5%, more preferably no more than about 3%, more preferably no more than about 2.5%, more preferably no more than about 2%, more preferably no more than about 1.5%, more preferably no more than about 1%, and most preferably no more than about 0.5%.

According to some aspects, the pharmaceutical composition may have an initial sugammadex mono chloro impurity concentration of no more than about 1%, more preferably no more than about 0.99%, more preferably no more than about 0.98%, more preferably no more than about 0.97%, more preferably no more than about 0.96%, more preferably no more than about 0.95%, more preferably no more than about 0.94%, more preferably no more than about 0.93%, more preferably no more than about 0.92%, more preferably no more than about 0.91%, more preferably no more than about 0.90%, more preferably no more than about 0.89%, more preferably no more than about 0.88%, more preferably no more than about 0.87%, more preferably no more than about 0.86%, more preferably no more than about 0.85%, more preferably no more than about 0.84%, more preferably no more than about 0.83%, more preferably no more than about 0.82%, more preferably no more than about 0.81%, more preferably no more than about 0.80%, more preferably no more than about 0.79%, more preferably no more than about 0.78%, more preferably no more than about 0.77%, more preferably no more than about 0.76%, more preferably no more than about 0.75%, more preferably no more than about 0.74%, more preferably no more than about 0.73%, more preferably no more than about 0.72%, more preferably no more than about 0.71%, more preferably no more than about 0.97%, more preferably no more than about 0.69%, more preferably no more than about 0.68%, more preferably no more than about 0.67%, more preferably no more than about 0.66%, more preferably no more than about 0.65%, more preferably no more than about 0.64%, more preferably no more than about 0.63%, more preferably no more than about 0.62%, more preferably no more than about 0.61%, more preferably no more than about 0.60%, more preferably no more than about 0.59%, more preferably no more than about 0.58%, more preferably no more than about 0.57%, more preferably no more than about 0.56%, more preferably no more than about 0.55%, more preferably no more than about 0.54%, more preferably no more than about 0.53%, more preferably no more than about 0.52%, more preferably no more than about 0.51%, more preferably no more than about 0.50%, more preferably no more than about 0.49%, more preferably no more than about 0.48%, more preferably no more than about 0.47%, more preferably no more than about 0.46%, more preferably no more than about 0.45%, more preferably no more than about 0.44%, more preferably no more than about 0.43%, more preferably no more than about 0.42%, more preferably no more than about 0.41%, more preferably no more than about 0.40%, more preferably no more than about 0.39%, more preferably no more than about 0.38%, more preferably no more than about 0.37%, more preferably no more than about 0.36%, more preferably no more than about 0.35%, more preferably no more than about 0.34%, more preferably no more than about 0.33%, more preferably no more than about 0.32%, more preferably no more than about 0.31%, more preferably no more than about 0.30%, more preferably no more than about 0.29%, more preferably no more than about 0.28%, more preferably no more than about 0.27%, more preferably no more than about 0.26%, more preferably no more than about 0.25%, more preferably no more than about 0.24%, more preferably no more than about 0.23%, more preferably no more than about 0.22%, more preferably no more than about 0.21%, more preferably no more than about 0.20%, more preferably no more than about 0.19%, more preferably no more than about 0.18%, more preferably no more than about 0.17%, more preferably no more than about 0.16%, more preferably no more than about 0.15%, more preferably no more than about 0.14%, more preferably no more than about 0.13%, more preferably no more than about 0.12%, more preferably no more than about 0.11%, more preferably no more than about 0.10%, more preferably no more than about 0.09%, more preferably no more than about 0.08%, more preferably no more than about 0.07%, more preferably no more than about 0.06%, more preferably no more than about 0.05%, more preferably no more than about 0.04%, more preferably no more than about 0.03%, more preferably no more than about 0.02%, and most preferably no more than about 0.01%.

According to some aspects, the pharmaceutical composition may have a sugammadex mono chloro impurity concentration after a certain period of shelf life of no more than about 5%, more preferably no more than about 4.5%, more preferably no more than about 4%, more preferably no more than about 3.5%, more preferably no more than about 3%, more preferably no more than about 2.5%, more preferably no more than about 2%, more preferably no more than about 1.5%, more preferably no more than about 1%, and most preferably no more than about 0.5%.

According to some aspects, the pharmaceutical composition may have a sugammadex mono chloro impurity concentration after a certain period of shelf life of no more than about 1%, more preferably no more than about 0.99%, more preferably no more than about 0.98%, more preferably no more than about 0.97%, more preferably no more than about 0.96%, more preferably no more than about 0.95%, more preferably no more than about 0.94%, more preferably no more than about 0.93%, more preferably no more than about 0.92%, more preferably no more than about 0.91%, more preferably no more than about 0.90%, more preferably no more than about 0.89%, more preferably no more than about 0.88%, more preferably no more than about 0.87%, more preferably no more than about 0.86%, more preferably no more than about 0.85%, more preferably no more than about 0.84%, more preferably no more than about 0.83%, more preferably no more than about 0.82%, more preferably no more than about 0.81%, more preferably no more than about 0.80%, more preferably no more than about 0.79%, more preferably no more than about 0.78%, more preferably no more than about 0.77%, more preferably no more than about 0.76%, more preferably no more than about 0.75%, more preferably no more than about 0.74%, more preferably no more than about 0.73%, more preferably no more than about 0.72%, more preferably no more than about 0.71%, more preferably no more than about 0.97%, more preferably no more than about 0.69%, more preferably no more than about 0.68%, more preferably no more than about 0.67%, more preferably no more than about 0.66%, more preferably no more than about 0.65%, more preferably no more than about 0.64%, more preferably no more than about 0.63%, more preferably no more than about 0.62%, more preferably no more than about 0.61%, more preferably no more than about 0.60%, more preferably no more than about 0.59%, more preferably no more than about 0.58%, more preferably no more than about 0.57%, more preferably no more than about 0.56%, more preferably no more than about 0.55%, more preferably no more than about 0.54%, more preferably no more than about 0.53%, more preferably no more than about 0.52%, more preferably no more than about 0.51%, more preferably no more than about 0.50%, more preferably no more than about 0.49%, more preferably no more than about 0.48%, more preferably no more than about 0.47%, more preferably no more than about 0.46%, more preferably no more than about 0.45%, more preferably no more than about 0.44%, more preferably no more than about 0.43%, more preferably no more than about 0.42%, more preferably no more than about 0.41%, more preferably no more than about 0.40%, more preferably no more than about 0.39%, more preferably no more than about 0.38%, more preferably no more than about 0.37%, more preferably no more than about 0.36%, more preferably no more than about 0.35%, more preferably no more than about 0.34%, more preferably no more than about 0.33%, more preferably no more than about 0.32%, more preferably no more than about 0.31%, more preferably no more than about 0.30%, more preferably no more than about 0.29%, more preferably no more than about 0.28%, more preferably no more than about 0.27%, more preferably no more than about 0.26%, more preferably no more than about 0.25%, more preferably no more than about 0.24%, more preferably no more than about 0.23%, more preferably no more than about 0.22%, more preferably no more than about 0.21%, more preferably no more than about 0.20%, more preferably no more than about 0.19%, more preferably no more than about 0.18%, more preferably no more than about 0.17%, more preferably no more than about 0.16%, more preferably no more than about 0.15%, more preferably no more than about 0.14%, more preferably no more than about 0.13%, more preferably no more than about 0.12%, more preferably no more than about 0.11%, more preferably no more than about 0.10%, more preferably no more than about 0.09%, more preferably no more than about 0.08%, more preferably no more than about 0.07%, more preferably no more than about 0.06%, more preferably no more than about 0.05%, more preferably no more than about 0.04%, more preferably no more than about 0.03%, more preferably no more than about 0.02%, and most preferably no more than about 0.01%.

According to some aspects, the pharmaceutical composition may have an initial sugammadex mono hydroxyl impurity concentration of no more than about 5%, more preferably no more than about 4.5%, more preferably no more than about 4%, more preferably no more than about 3.5%, more preferably no more than about 3%, more preferably no more than about 2.5%, more preferably no more than about 2%, more preferably no more than about 1.5%, more preferably no more than about 1%, and most preferably no more than about 0.5%.

According to some aspects, the pharmaceutical composition may have an initial sugammadex mono hydroxyl impurity concentration of no more than about 1%, more preferably no more than about 0.99%, more preferably no more than about 0.98%, more preferably no more than about 0.97%, more preferably no more than about 0.96%, more preferably no more than about 0.95%, more preferably no more than about 0.94%, more preferably no more than about 0.93%, more preferably no more than about 0.92%, more preferably no more than about 0.91%, more preferably no more than about 0.90%, more preferably no more than about 0.89%, more preferably no more than about 0.88%, more preferably no more than about 0.87%, more preferably no more than about 0.86%, more preferably no more than about 0.85%, more preferably no more than about 0.84%, more preferably no more than about 0.83%, more preferably no more than about 0.82%, more preferably no more than about 0.81%, more preferably no more than about 0.80%, more preferably no more than about 0.79%, more preferably no more than about 0.78%, more preferably no more than about 0.77%, more preferably no more than about 0.76%, more preferably no more than about 0.75%, more preferably no more than about 0.74%, more preferably no more than about 0.73%, more preferably no more than about 0.72%, more preferably no more than about 0.71%, more preferably no more than about 0.97%, more preferably no more than about 0.69%, more preferably no more than about 0.68%, more preferably no more than about 0.67%, more preferably no more than about 0.66%, more preferably no more than about 0.65%, more preferably no more than about 0.64%, more preferably no more than about 0.63%, more preferably no more than about 0.62%, more preferably no more than about 0.61%, more preferably no more than about 0.60%, more preferably no more than about 0.59%, more preferably no more than about 0.58%, more preferably no more than about 0.57%, more preferably no more than about 0.56%, more preferably no more than about 0.55%, more preferably no more than about 0.54%, more preferably no more than about 0.53%, more preferably no more than about 0.52%, more preferably no more than about 0.51%, more preferably no more than about 0.50%, more preferably no more than about 0.49%, more preferably no more than about 0.48%, more preferably no more than about 0.47%, more preferably no more than about 0.46%, more preferably no more than about 0.45%, more preferably no more than about 0.44%, more preferably no more than about 0.43%, more preferably no more than about 0.42%, more preferably no more than about 0.41%, more preferably no more than about 0.40%, more preferably no more than about 0.39%, more preferably no more than about 0.38%, more preferably no more than about 0.37%, more preferably no more than about 0.36%, more preferably no more than about 0.35%, more preferably no more than about 0.34%, more preferably no more than about 0.33%, more preferably no more than about 0.32%, more preferably no more than about 0.31%, more preferably no more than about 0.30%, more preferably no more than about 0.29%, more preferably no more than about 0.28%, more preferably no more than about 0.27%, more preferably no more than about 0.26%, more preferably no more than about 0.25%, more preferably no more than about 0.24%, more preferably no more than about 0.23%, more preferably no more than about 0.22%, more preferably no more than about 0.21%, more preferably no more than about 0.20%, more preferably no more than about 0.19%, more preferably no more than about 0.18%, more preferably no more than about 0.17%, more preferably no more than about 0.16%, more preferably no more than about 0.15%, more preferably no more than about 0.14%, more preferably no more than about 0.13%, more preferably no more than about 0.12%, more preferably no more than about 0.11%, more preferably no more than about 0.10%, more preferably no more than about 0.09%, more preferably no more than about 0.08%, more preferably no more than about 0.07%, more preferably no more than about 0.06%, more preferably no more than about 0.05%, more preferably no more than about 0.04%, more preferably no more than about 0.03%, more preferably no more than about 0.02%, and most preferably no more than about 0.01%.

According to some aspects, the pharmaceutical composition may have a sugammadex mono hydroxyl impurity concentration after a certain period of shelf life of no more than about 5%, more preferably no more than about 4.5%, more preferably no more than about 4%, more preferably no more than about 3.5%, more preferably no more than about 3%, more preferably no more than about 2.5%, more preferably no more than about 2%, more preferably no more than about 1.5%, more preferably no more than about 1%, and most preferably no more than about 0.5%.

According to some aspects, the pharmaceutical composition may have a sugammadex mono hydroxyl impurity concentration after a certain period of shelf life of no more than about 1%, more preferably no more than about 0.99%, more preferably no more than about 0.98%, more preferably no more than about 0.97%, more preferably no more than about 0.96%, more preferably no more than about 0.95%, more preferably no more than about 0.94%, more preferably no more than about 0.93%, more preferably no more than about 0.92%, more preferably no more than about 0.91%, more preferably no more than about 0.90%, more preferably no more than about 0.89%, more preferably no more than about 0.88%, more preferably no more than about 0.87%, more preferably no more than about 0.86%, more preferably no more than about 0.85%, more preferably no more than about 0.84%, more preferably no more than about 0.83%, more preferably no more than about 0.82%, more preferably no more than about 0.81%, more preferably no more than about 0.80%, more preferably no more than about 0.79%, more preferably no more than about 0.78%, more preferably no more than about 0.77%, more preferably no more than about 0.76%, more preferably no more than about 0.75%, more preferably no more than about 0.74%, more preferably no more than about 0.73%, more preferably no more than about 0.72%, more preferably no more than about 0.71%, more preferably no more than about 0.97%, more preferably no more than about 0.69%, more preferably no more than about 0.68%, more preferably no more than about 0.67%, more preferably no more than about 0.66%, more preferably no more than about 0.65%, more preferably no more than about 0.64%, more preferably no more than about 0.63%, more preferably no more than about 0.62%, more preferably no more than about 0.61%, more preferably no more than about 0.60%, more preferably no more than about 0.59%, more preferably no more than about 0.58%, more preferably no more than about 0.57%, more preferably no more than about 0.56%, more preferably no more than about 0.55%, more preferably no more than about 0.54%, more preferably no more than about 0.53%, more preferably no more than about 0.52%, more preferably no more than about 0.51%, more preferably no more than about 0.50%, more preferably no more than about 0.49%, more preferably no more than about 0.48%, more preferably no more than about 0.47%, more preferably no more than about 0.46%, more preferably no more than about 0.45%, more preferably no more than about 0.44%, more preferably no more than about 0.43%, more preferably no more than about 0.42%, more preferably no more than about 0.41%, more preferably no more than about 0.40%, more preferably no more than about 0.39%, more preferably no more than about 0.38%, more preferably no more than about 0.37%, more preferably no more than about 0.36%, more preferably no more than about 0.35%, more preferably no more than about 0.34%, more preferably no more than about 0.33%, more preferably no more than about 0.32%, more preferably no more than about 0.31%, more preferably no more than about 0.30%, more preferably no more than about 0.29%, more preferably no more than about 0.28%, more preferably no more than about 0.27%, more preferably no more than about 0.26%, more preferably no more than about 0.25%, more preferably no more than about 0.24%, more preferably no more than about 0.23%, more preferably no more than about 0.22%, more preferably no more than about 0.21%, more preferably no more than about 0.20%, more preferably no more than about 0.19%, more preferably no more than about 0.18%, more preferably no more than about 0.17%, more preferably no more than about 0.16%, more preferably no more than about 0.15%, more preferably no more than about 0.14%, more preferably no more than about 0.13%, more preferably no more than about 0.12%, more preferably no more than about 0.11%, more preferably no more than about 0.10%, more preferably no more than about 0.09%, more preferably no more than about 0.08%, more preferably no more than about 0.07%, more preferably no more than about 0.06%, more preferably no more than about 0.05%, more preferably no more than about 0.04%, more preferably no more than about 0.03%, more preferably no more than about 0.02%, and most preferably no more than about 0.01%.

According to some aspects, the pharmaceutical composition may have an initial unknown impurity concentration of no more than about 5%, more preferably no more than about 4.5%, more preferably no more than about 4%, more preferably no more than about 3.5%, more preferably no more than about 3%, more preferably no more than about 2.5%, more preferably no more than about 2%, more preferably no more than about 1.5%, more preferably no more than about 1%, and most preferably no more than about 0.5%.

According to some aspects, the pharmaceutical composition may have an initial unknown impurity concentration of no more than about 1%, more preferably no more than about 0.99%, more preferably no more than about 0.98%, more preferably no more than about 0.97%, more preferably no more than about 0.96%, more preferably no more than about 0.95%, more preferably no more than about 0.94%, more preferably no more than about 0.93%, more preferably no more than about 0.92%, more preferably no more than about 0.91%, more preferably no more than about 0.90%, more preferably no more than about 0.89%, more preferably no more than about 0.88%, more preferably no more than about 0.87%, more preferably no more than about 0.86%, more preferably no more than about 0.85%, more preferably no more than about 0.84%, more preferably no more than about 0.83%, more preferably no more than about 0.82%, more preferably no more than about 0.81%, more preferably no more than about 0.80%, more preferably no more than about 0.79%, more preferably no more than about 0.78%, more preferably no more than about 0.77%, more preferably no more than about 0.76%, more preferably no more than about 0.75%, more preferably no more than about 0.74%, more preferably no more than about 0.73%, more preferably no more than about 0.72%, more preferably no more than about 0.71%, more preferably no more than about 0.97%, more preferably no more than about 0.69%, more preferably no more than about 0.68%, more preferably no more than about 0.67%, more preferably no more than about 0.66%, more preferably no more than about 0.65%, more preferably no more than about 0.64%, more preferably no more than about 0.63%, more preferably no more than about 0.62%, more preferably no more than about 0.61%, more preferably no more than about 0.60%, more preferably no more than about 0.59%, more preferably no more than about 0.58%, more preferably no more than about 0.57%, more preferably no more than about 0.56%, more preferably no more than about 0.55%, more preferably no more than about 0.54%, more preferably no more than about 0.53%, more preferably no more than about 0.52%, more preferably no more than about 0.51%, more preferably no more than about 0.50%, more preferably no more than about 0.49%, more preferably no more than about 0.48%, more preferably no more than about 0.47%, more preferably no more than about 0.46%, more preferably no more than about 0.45%, more preferably no more than about 0.44%, more preferably no more than about 0.43%, more preferably no more than about 0.42%, more preferably no more than about 0.41%, more preferably no more than about 0.40%, more preferably no more than about 0.39%, more preferably no more than about 0.38%, more preferably no more than about 0.37%, more preferably no more than about 0.36%, more preferably no more than about 0.35%, more preferably no more than about 0.34%, more preferably no more than about 0.33%, more preferably no more than about 0.32%, more preferably no more than about 0.31%, more preferably no more than about 0.30%, more preferably no more than about 0.29%, more preferably no more than about 0.28%, more preferably no more than about 0.27%, more preferably no more than about 0.26%, more preferably no more than about 0.25%, more preferably no more than about 0.24%, more preferably no more than about 0.23%, more preferably no more than about 0.22%, more preferably no more than about 0.21%, more preferably no more than about 0.20%, more preferably no more than about 0.19%, more preferably no more than about 0.18%, more preferably no more than about 0.17%, more preferably no more than about 0.16%, more preferably no more than about 0.15%, more preferably no more than about 0.14%, more preferably no more than about 0.13%, more preferably no more than about 0.12%, more preferably no more than about 0.11%, more preferably no more than about 0.10%, more preferably no more than about 0.09%, more preferably no more than about 0.08%, more preferably no more than about 0.07%, more preferably no more than about 0.06%, more preferably no more than about 0.05%, more preferably no more than about 0.04%, more preferably no more than about 0.03%, more preferably no more than about 0.02%, and most preferably no more than about 0.01%.

According to some aspects, the pharmaceutical composition may have an unknown impurity concentration after a certain period of shelf life of no more than about 5%, more preferably no more than about 4.5%, more preferably no more than about 4%, more preferably no more than about 3.5%, more preferably no more than about 3%, more preferably no more than about 2.5%, more preferably no more than about 2%, more preferably no more than about 1.5%, more preferably no more than about 1%, and most preferably no more than about 0.5%.

According to some aspects, the pharmaceutical composition may have an unknown impurity concentration after a certain period of shelf life of no more than about 1%, more preferably no more than about 0.99%, more preferably no more than about 0.98%, more preferably no more than about 0.97%, more preferably no more than about 0.96%, more preferably no more than about 0.95%, more preferably no more than about 0.94%, more preferably no more than about 0.93%, more preferably no more than about 0.92%, more preferably no more than about 0.91%, more preferably no more than about 0.90%, more preferably no more than about 0.89%, more preferably no more than about 0.88%, more preferably no more than about 0.87%, more preferably no more than about 0.86%, more preferably no more than about 0.85%, more preferably no more than about 0.84%, more preferably no more than about 0.83%, more preferably no more than about 0.82%, more preferably no more than about 0.81%, more preferably no more than about 0.80%, more preferably no more than about 0.79%, more preferably no more than about 0.78%, more preferably no more than about 0.77%, more preferably no more than about 0.76%, more preferably no more than about 0.75%, more preferably no more than about 0.74%, more preferably no more than about 0.73%, more preferably no more than about 0.72%, more preferably no more than about 0.71%, more preferably no more than about 0.97%, more preferably no more than about 0.69%, more preferably no more than about 0.68%, more preferably no more than about 0.67%, more preferably no more than about 0.66%, more preferably no more than about 0.65%, more preferably no more than about 0.64%, more preferably no more than about 0.63%, more preferably no more than about 0.62%, more preferably no more than about 0.61%, more preferably no more than about 0.60%, more preferably no more than about 0.59%, more preferably no more than about 0.58%, more preferably no more than about 0.57%, more preferably no more than about 0.56%, more preferably no more than about 0.55%, more preferably no more than about 0.54%, more preferably no more than about 0.53%, more preferably no more than about 0.52%, more preferably no more than about 0.51%, more preferably no more than about 0.50%, more preferably no more than about 0.49%, more preferably no more than about 0.48%, more preferably no more than about 0.47%, more preferably no more than about 0.46%, more preferably no more than about 0.45%, more preferably no more than about 0.44%, more preferably no more than about 0.43%, more preferably no more than about 0.42%, more preferably no more than about 0.41%, more preferably no more than about 0.40%, more preferably no more than about 0.39%, more preferably no more than about 0.38%, more preferably no more than about 0.37%, more preferably no more than about 0.36%, more preferably no more than about 0.35%, more preferably no more than about 0.34%, more preferably no more than about 0.33%, more preferably no more than about 0.32%, more preferably no more than about 0.31%, more preferably no more than about 0.30%, more preferably no more than about 0.29%, more preferably no more than about 0.28%, more preferably no more than about 0.27%, more preferably no more than about 0.26%, more preferably no more than about 0.25%, more preferably no more than about 0.24%, more preferably no more than about 0.23%, more preferably no more than about 0.22%, more preferably no more than about 0.21%, more preferably no more than about 0.20%, more preferably no more than about 0.19%, more preferably no more than about 0.18%, more preferably no more than about 0.17%, more preferably no more than about 0.16%, more preferably no more than about 0.15%, more preferably no more than about 0.14%, more preferably no more than about 0.13%, more preferably no more than about 0.12%, more preferably no more than about 0.11%, more preferably no more than about 0.10%, more preferably no more than about 0.09%, more preferably no more than about 0.08%, more preferably no more than about 0.07%, more preferably no more than about 0.06%, more preferably no more than about 0.05%, more preferably no more than about 0.04%, more preferably no more than about 0.03%, more preferably no more than about 0.02%, and most preferably no more than about 0.01%.

According to some aspects, the unknown impurity may be an impurity observed at about RRT 1.12 according to the HPLC technique described in Example VII.

As used throughout this application, the term "shelf life" refers to the length of time that a product may be stored without becoming unfit for medical use. Examples of compositions which are unfit for medical use include, but are not limited to, compositions with unacceptably high impurity levels and/or the presence of physical changes such as color change and/or the presence of insoluble particles. "Shelf life" can, for example, be determined as set forth in the U.S. Food and Drug Administration's Guidance for Industry: Q1E Evaluation of Stability Data (June 2004), the contents of which are hereby incorporated by reference.

The period of shelf life of the pharmaceutical composition may be 1 week, preferably 2 weeks, preferably 3 weeks, preferably 1 month, preferably 2 months, more preferably 3 months, more preferably 4 months, more preferably 5 months, more preferably 6 months, more preferably 7 months, more preferably 8 months, more preferably 9 months, more preferably 10 months, more preferably 11 months, more 12 months, preferably 13 months, more preferably 14 months, more preferably 15 months, more preferably 16 months, more preferably 17 months, more preferably 18 months, more preferably 19 months, more preferably 20 months, more preferably 21 months, more preferably 22 months, more preferably 23 months, more preferably 24 months, more preferably 25 months, more preferably 26 months, more preferably 27 months, more preferably 28 months, more preferably 29 months, more preferably 30 months, more preferably 31 months, more preferably 32 months, more preferably 33 months, more preferably 34 months, more preferably 35 months, and most preferably 36 months. According to some aspects, the period of shelf life may vary based on product presentation.

Shelf life may be determined by measuring certain characteristics of the composition that may indicate that the composition is unfit for medical use. For example, shelf life may be determined by measuring the concentration of impurities in the pharmaceutical composition after storage at 25° C. and 60% relative humidity. In another example, shelf life may be determined by measuring the concentration of impurities in the composition after storage at 40° C. and 75% relative humidity.

According to some aspects, shelf life may be attributed at least in part to the concentration of impurities in the composition such that the reduction of impurity concentration and/or rate of impurity formation lengthens the composition's shelf life.

According to some aspects, the pharmaceutical composition is sterile. As used herein, "sterile" refers to meeting sterility requirements for injection into the human body. According to some aspects, sterility may require passing results when measured via the membrane filtration method and/or direct inoculation method as set forth in USP chapter <71>.

The pharmaceutical composition may be provided in a pre-filled syringe. In some examples, the pre-filled syringe may comprise a plunger stopper, a barrel, a needle adapter, a needle hub, and a needle suitable for injection. According to some aspects, the pre-filled syringe may comprise glass, rubber, or a combination thereof, such as a glass barrel and a rubber plunger stopper.

The pre-filled syringe may have a labeled size. As used herein, the term "labeled size" refers to the pre-filled syringe's pharmaceutical composition holding capacity and is equal to the volume of a pharmaceutical composition containable in the pre-filled syringe. The pre-filled syringe may have a labeled size of 0.5 mL, optionally 1 mL, optionally 1.5 mL, optionally 2 mL, optionally 2.5 mL, optionally 3 mL, optionally 3.5 mL, optionally 4 mL, optionally 4.5 mL, optionally 5 mL, optionally 5.5 mL, optionally 6 mL, optionally 6.5 mL, optionally 7 mL, optionally 7.5 mL, optionally 8 mL, optionally 8.5 mL, optionally 9 mL, optionally 9.5 mL, and optionally 10 mL.

According to some aspects, the pre-filled syringe may have an acceptable headspace. As used herein, the term "headspace" refers to the volume of a container unoccupied by a product (such as a pharmaceutical composition) contained in the container, and may alternatively be referred to herein as "excess fill volume." It should be understood that in the case of a container containing a liquid product, the headspace may correspond to the volume of gas contained in the container.

According to some aspects, an acceptable headspace may correspond to a headspace that provides an acceptable impurity level after a certain period of shelf life as described herein. For example, an acceptable headspace may be a headspace having a volume that, when filled with air, has an oxygen content that limits oxidation of the active agent contained in the container after a certain period of shelf life to a level sufficient to provide an impurity level after the period of shelf life as described herein.

According to some aspects, an acceptable headspace may depend on the size of the container. For example, an acceptable headspace in a pre-filled syringe may be a headspace that is less than the USP <1151> Pharmaceutical Dosage Forms recommendations for excess fill volume for injectable systems, specifically as shown in Table 1.

TABLE 1

Example Acceptable Headspace Volume Per Labeled Pre-Filled Syringe Size

| Labeled Size of Pre-Filled Syringe | Acceptable Headspace Volume | |
|---|---|---|
| (mL) | For Mobile Liquids (mL) | For Viscous Liquids (mL) |
| 0.5 | <0.10 | <0.12 |
| 1.0 | <0.10 | <0.15 |
| 2.0 | <0.15 | <0.25 |
| 5.0 | <0.30 | <0.50 |
| 10.0 | <0.50 | <0.70 |
| 20.0 | <0.60 | <0.90 |
| 30.0 | <0.80 | <1.20 |
| 50.0 or more | <2% | <3% |

According to some aspects, for a pre-filled syringe having a labeled size of 2 mL, an acceptable headspace may be less than about 0.15 mL, optionally less than about 0.14 mL, optionally less than about 0.13 mL, optionally less than about 0.12 mL, optionally less than about 0.11 mL, optionally less than about 0.10 mL, optionally less than about 0.09 mL, optionally less than about 0.08 mL, optionally less than about 0.07 mL, optionally less than about 0.06 mL, optionally less than about 0.05 mL, optionally less than about 0.04 mL, optionally less than about 0.03 mL, optionally less than about 0.02 mL, and optionally less than about 0.01 mL.

According to some aspects, for a pre-filled syringe having a labeled size of 5 mL, an acceptable headspace may be less than about 0.30 mL, optionally less than about 0.29 mL, optionally less than about 0.28 mL, optionally less than about 0.27 mL, optionally less than about 0.26 mL, optionally less than about 0.25 mL, optionally less than about 0.24 mL, optionally less than about 0.23 mL, optionally less than about 0.22 mL, optionally less than about 0.21 mL, optionally less than about 0.20 mL, optionally less than about 0.19 mL, optionally less than about 0.18 mL, optionally less than about 0.17 mL, optionally less than about 0.16 mL, optionally less than about 0.15 mL, optionally less than about 0.14 mL, optionally less than about 0.13 mL, optionally less than about 0.12 mL, optionally less than about 0.11 mL, optionally less than about 0.10 mL, optionally less than about 0.09 mL, optionally less than about 0.08 mL, optionally less than about 0.07 mL, optionally less than about 0.06 mL, optionally less than about 0.05 mL, optionally less than about 0.04 mL, optionally less than about 0.03 mL, optionally less than about 0.02 mL, and optionally less than about 0.01 mL.

According to some aspects, the headspace may contain atmospheric air. As used herein, the term "atmospheric air" refers to the natural atmosphere surrounding the earth. According to some aspects, atmospheric air may comprise nitrogen, oxygen, argon, and/or carbon dioxide. In one non-limiting example, atmospheric air may comprise about 78.084% (v/v) nitrogen, about 20.946% (v/v) oxygen, about 0.934% (v/v) argon, about 0.033% (v/v) carbon dioxide, and about 0.003% (v/v) of other gases. Additionally or alternatively, the headspace may comprise or consist of an inert gas (such as nitrogen) and/or carbon dioxide.

According to some aspects, the pre-filled syringe may have a headspace with a volume that is less than about 8% of the pre-filled syringe's labeled size, optionally less than about 7.5%, optionally less than about 7%, optionally less than about 6.5%, optionally less than about 6%, optionally less than about 5.5%, optionally less than about 5%, optionally less than about 4.5%, optionally less than about 4%, optionally less than about 3.5%, optionally less than about 3%, optionally less than about 2.5%, optionally less than about 2%, optionally less than about 1.5%, optionally less than about 1%, optionally less than about 0.5%, optionally less than about 0.1%, and optionally less than about 0.01%.

The present disclosure is directed to a method for providing a sterile pharmaceutical composition as described herein. The method may comprise a preparation step, a filtration step, and a containment step. It should be understood that as used herein, the term "step" is not particularly limiting. For example, each step as described herein may be a discrete step such that steps are performed sequentially upon completion of a preceding step. Alternatively, at least a portion of the method may be continuous, or the steps may be performed out of the order stated.

The preparation step may comprise a solvent processing step, wherein the solvent is processed for use as described herein. For example, the solvent processing step may comprise reducing the dissolved oxygen level of a solvent or vehicle, such as WFI, by providing the solvent or vehicle in a first manufacturing tank and purging/sparging the solvent with an inert gas such as nitrogen gas such that the dissolved oxygen content is within an acceptable range. FIG. 1 shows an example first manufacturing tank 101 provided with a stirring mechanism 102.

According to some aspects, the solvent processing step may comprise maintaining the solvent at an acceptable temperature, such as a temperature standard to continuous circulation processes. In one non-limiting example, the solvent may be maintained at a temperature of about 80° C. for at least a portion of the solvent processing step.

The solvent processing step may comprise one or more qualitative and/or quantitative measurements. For example, the solvent processing step may comprise measuring the dissolved oxygen level of the solvent before, during, and/or after purging as described herein. Additionally or alternatively, the solvent processing step may comprise a Bacterial Endotoxins Test (BET). As used herein, a "Bacterial Endotoxins Test" or "BET" refers to an in vitro assay for detection and quantitation of bacterial endotoxins. According to some aspects, the BET may be performed using a gel clot technique or a photometric technique as specified in USP chapter <85> and/or as known in the field of microbiological testing of injectable products. According to some aspects, the method requires obtaining a satisfactory result from the one or more qualitative and/or quantitative measurements before proceeding to the next step of the process.

According to some aspects, the preparation step may comprise a solubilizing step wherein the active agent is solubilized in the solvent. The solubilizing step may comprise solubilizing an active agent as described herein in all or a portion of the solvent from the solvent processing step.

For example, FIG. 1 shows an example second manufacturing tank 103 in communication with the first manufacturing tank 101. Second manufacturing tank 103 may be provided with a stirring mechanism 104, such as a stirrer. All or a portion of the solvent from the first manufacturing tank 101 may be transferred to the second manufacturing tank 102. For example, from about 50 to 100% (w/w) of the solvent from the first manufacturing tank 101 may be transferred to the second manufacturing tank 102, optionally from about 60 to 100% (w/w), optionally from about 70 to 100% (w/w), optionally from about 85 to 95% (w/w), and optionally about 90% (w/w).

According to some aspects, the solvent in the second manufacturing tank 102 may be cooled to room temperature prior to and/or simultaneously with solubilizing the active agent therein. As used herein, "room temperature" refers to a temperature of between about 20 to 25° C.

According to some aspects, the solvent in the second manufacturing tank 102 may be processed as described herein prior to and/or simultaneously with solubilizing the active agent therein. For example, the solvent in the second manufacturing tank 102 may be purged with nitrogen gas such that the dissolved oxygen content is within an acceptable range prior to and/or simultaneously with solubilizing the active agent therein.

The active agent may be solubilized in the solvent in the second manufacturing tank 102 to provide an active agent concentration as described herein. Alternatively, the preparation step may comprise providing the active agent concentration as described herein by adding additional solvent to the second manufacturing tank 102 after the active agent has been solubilized.

According to some aspects, the preparation step may comprise a pH-adjustment step. The pH-adjustment step may comprise combining the solvent having the active agent solubilized therein with a pH adjusting agent as described herein until the solution has a pH as described herein. For example, after an acceptable solubilized active agent concentration has been provided in the second manufacturing tank 102, the method may comprise adding a pH adjusting agent to the second manufacturing tank 102 in order to obtain a pH as described herein.

According to some aspects, all or a portion of the preparation step may part of a "non-sterile phase." As used herein, the term "non-sterile phase" refers to a phase of the method as described herein wherein all or a portion of the pharmaceutical composition's components are not required to be sterile.

The method may comprise a filtration step wherein the solvent having the active agent and the pH adjusting agent solubilized therein is passed through one or more filters. For example, as shown in FIG. 1, the solvent having the active agent and the pH adjusting agent solubilized therein may be passed from the second manufacturing tank 102 through a filter 105 and into a third manufacturing tank 106, wherein the third manufacturing tank 106 may be provided with a stirring mechanism such as a stirrer 107. It should be understood that while the example shown in FIG. 1 includes one filter 105, the method may comprise passing the solvent having the active agent and the pH adjusting agent solubilized therein through two, three, four, or more filters, wherein each of the filters is independently the same as or different from another filter used in the method.

According to some aspects, the one or more filters may be sufficient to provide a sterile pharmaceutical composition as described herein. For example, each of the one or more filters may independently be a sterilizing-grade filter comprising a membrane having an average pore size of between about 0.1 and 1 μm, optionally between about 0.2 and 1 μm, optionally between about 0.2 and 0.45 μm, optionally about 0.45 μm, and optionally about 0.2 μm. According to some aspects, each of the one or more filters may independently comprise a membrane having pores rated for mycoplasma and/or other small microbes. Example materials useful for the one or more filters include, but are not limited to, regenerated cellulose, polymers such as polyethersulfone (PES), polyvinylidene fluoride (PVDF), and polytetrafluoroethylene (PTFE), and combinations thereof. Non-limiting examples of sterilizing-grade filters useful according to the present disclosure include Merck's OptiScale® 25 Milligard PES 1.2/0.45 μm NB and Merck's Millipore Express® SHF 2.0 Capsule Filter. According to some aspects, the method may comprise passing the solvent having the active agent and the pH adjusting agent solubilized therein through a filter combination comprising Merck's OptiScale® 25 Milligard PES 1.2/0.45 μm NB and Merck's Millipore Express® SHF 2.0 Capsule Filter.

According to some aspects, passing the solvent having the active agent and the pH adjusting agent solubilized therein through the filter may represent passage from the non-sterile phase of the method to a sterile phase of the method. As used herein, the term "sterile phase" refers to a phase of the method as described herein wherein the pharmaceutical composition is sterile.

The method may comprise a containment step wherein the sterile pharmaceutical composition is provided in a container as described herein, such as in a pre-filled syringe or a component thereof (e.g., in a barrel of a pre-filled syringe). Containing the sterile pharmaceutical composition in the container and/or component thereof may be accomplished using any machinery known in the art capable of filling a pre-filled syringe and/or component thereof with a sterile pharmaceutical solution as described herein.

As shown in FIG. 1, prior to filling one or more pre-filled syringes and/or a components thereof with the sterile pharmaceutical composition using machinery 109, the sterile pharmaceutical composition may be held as a sterile bulk in the third manufacturing tank 106 and/or in a buffer tank 108. The sterile pharmaceutical composition may be held as a sterile bulk in the third manufacturing tank 106 and/or in the buffer tank 108 for a time sufficient to maintain a continuous transfer throughout the process as described herein. For example, the sterile pharmaceutical composition may be held as a sterile bulk in the third manufacturing tank 106 and/or in the buffer tank 108 from one minute to about two hours, optionally from about thirty to about ninety minutes, and optionally for about one hour.

According to some aspects, a second filter (not shown) as described herein may be provided between the third manufacturing tank 106 and the buffer tank 108 such that the pharmaceutical composition passes through the filter as it is transferred from the third manufacturing tank to the buffer tank 108.

The containment step may comprise a stoppering step wherein each pre-filled syringe is provided with a stopper sufficient to provide a headspace as described herein. According to some aspects, the stopper is a plunger stopper as described herein. In this example, the stoppering step may comprise providing a plunger stopper into the barrel of the pre-filed syringe sufficient to provide a headspace as described herein. The stopper may be provided manually, via a vacuum, or a combination thereof.

The method may further comprise one or more additional steps, such as a visual inspection step to confirm the propriety of the product and/or a labelling step, as shown in FIG. 1.

According to some aspects, one or more of the steps described herein may be performed at a temperature such that the pharmaceutical composition and/or components thereof are maintained below a threshold temperature. The threshold temperature may be a temperature insufficient to provide an impurity level as described herein. For example, in the case of a pharmaceutical composition containing sugammadex sodium as described herein, the threshold temperature may be a temperature above which sugammadex sodium degradation occurs at an unacceptable rate and/or to an unacceptable level. The threshold temperature may be a temperature above which conventional steam sterilization processes or other heat-based sterilization processes are performed, as it has been found that the temperature required by terminal sterilization often induces and/or exaggerates impurity formation in sugammadex sodium-containing products, which impacts the product's stability and thus, shelf life.

Example threshold temperatures include, but are not limited to, about 121° C., optionally about 110° C., and optionally about 100° C. According to some aspects, the threshold temperature may be about 121° C., optionally about 120° C., optionally about 119° C., optionally about 118° C., optionally about 117° C., optionally about 116° C., optionally about 115° C., optionally about 114° C., optionally about 113° C., optionally about 112° C., optionally about 111° C., optionally about 110° C.

According to some aspects, the method may be free of any heat-based sterilization processes. As used herein, the term a "heat-based sterilization process" is a process intended to sterilize a pharmaceutical composition that includes subjecting the pharmaceutical composition to a temperature at or above a threshold temperature as described herein. One non-limiting example of a heat-based sterilization process includes a steam sterilization process.

While the aspects described herein have been described in conjunction with the example aspects outlined above, various alternatives, modifications, variations, improvements, and/or substantial equivalents, whether known or that are or may be presently unforeseen, may become apparent to those having at least ordinary skill in the art. Accordingly, the example aspects, as set forth above, are intended to be illustrative, not limiting. Various changes may be made without departing from the spirit and scope of the disclosure. Therefore, the disclosure is intended to embrace all known or later-developed alternatives, modifications, variations, improvements, and/or substantial equivalents.

Thus, the claims are not intended to be limited to the aspects shown herein, but are to be accorded the full scope consistent with the language of the claims, where reference to an element in the singular is not intended to mean "one and only one" unless specifically so stated, but rather "one or more." All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed as a means plus function unless the element is expressly recited using the phrase "means for."

Further, the word "example" is used herein to mean "serving as an example, instance, or illustration." Any aspect described herein as "example" is not necessarily to be construed as preferred or advantageous over other aspects. Unless specifically stated otherwise, the term "some" refers to one or more. Combinations such as "at least one of A, B, or C," "at least one of A, B, and C," and "A, B, C, or any combination thereof" include any combination of A, B, and/or C, and may include multiples of A, multiples of B, or multiples of C. Specifically, combinations such as "at least one of A, B, or C," "at least one of A, B, and C," and "A, B, C, or any combination thereof" may be A only, B only, C only, A and B, A and C, B and C, or A and B and C, where any such combinations may contain one or more member or members of A, B, or C. Nothing disclosed herein is intended to be dedicated to the public regardless of whether such disclosure is explicitly recited in the claims.

The word "about" is used herein to mean within ±5% of the stated value, optionally within ±4%, optionally within ±3%, optionally within ±2%, optionally within ±1%, optionally within ±0.5%, optionally within ±0.1%, and optionally within ±0.01%.

The following examples are put forth so as to provide those of ordinary skill in the art with a complete disclosure and description of how to make and use the present invention, and are not intended to limit the scope of what the inventors regard as their invention nor are they intended to represent that the experiments described below are all or the only experiments performed. Efforts have been made to ensure accuracy with respect to numbers used (e.g. amounts, dimensions, etc.) but some experimental errors and deviations should be accounted for.

EXAMPLES

Example I: Preparation of a Sterile Pharmaceutical Composition

First, 100% of the batch size WFI was provided in a first manufacturing tank with stirring and was purged/sparged with nitrogen gas ($N_2$). Then, 90% of the WFI from the first manufacturing tank was transferred to a second manufacturing tank with stirring. In the second manufacturing tank, sugammadex sodium was solubilized in the WFI. The pH of the solution was then brought to 7.57 with HCl and NaOH. The volume of the second manufacturing tank was made to 100% of the batch size using WFI. The concentration of sugammadex sodium was about 108.8 mg/mL.

The solution was then passed through a filter combination of Merck's OptiScale® 25 Milligard PES 1.2/0.45 µm NB followed by Merck's Millipore Express® SHF 2.0 Capsule Filter into a third manufacturing tank using nitrogen pressure. The sterilized solution was then passed to and held in a buffer tank before the start of the filling operation. The sterilized solution was then transferred into 2 mL glass pre-filled syringe barrels. Each of the barrels was stoppered with a rubber plunger stopper sufficient to provide approximately no headspace. Each syringe was visually inspected after stoppering.

Comparative Example II: Preparation of Sterile Pharmaceutical Composition

First, 100% of the batch size WFI was provided in a first manufacturing tank with stirring and was purged/sparged with nitrogen gas ($N_2$). Then, 90% of the WFI from the first manufacturing tank was transferred to a second manufacturing tank with stirring. In the second manufacturing tank, sugammadex sodium was solubilized in the WFI. The pH of the solution was then brought to 7.57 with HCl and NaOH. The volume of the second manufacturing tank was made to 100% of the batch size using WFI. The concentration of sugammadex sodium was about 108.8 mg/mL.

The solution was then passed through a filter combination of Merck's OptiScale® 25 Milligard PES 1.2/0.45 µm NB followed by Merck's Millipore Express® SHF 2.0 Capsule Filter into a third manufacturing tank with stirring. The sterilized solution was then passed to and held in a buffer tank before the start of the filling operation. The sterilized solution was then transferred into 2 mL glass pre-filled syringe barrels. Each of the barrels was stoppered with a rubber plunger stopper sufficient to provide approximately no headspace, and each syringe was visually inspected after stoppering. The resulting pre-filled syringes were then subjected to a terminal moist heat sterilization process comprising exposing the pre-filled syringes to a temperature of not less than 121.4° C. for not less than 20 minutes in an autoclave.

Example III: Impurity Concentrations of Sterile Pharmaceutical Compositions

First, 102 pre-filled syringe units prepared according to Example I and 102 pre-filled syringe units prepared according to Comparative Example II were visually observed and then measured for pH. The pre-filled syringe units were also measured for s-oxide diastereomer-1 impurity, s-oxide diastereomer-2 impurity, impurity at ~1.12 RRT, mono chloro impurity, unknown impurities, and mono hydroxyl impurity concentrations by HPLC technique as described in Example VII. The results were compared with identical measurements for BRIDION® 2 mL single-dose glass vials containing 200 mg of mL sugammadex. The results of this study are shown in Table 2.

TABLE 2

|  | RLD (BRIDION®) Batch No: S019844 Expiry: April 2022 | Example I | Comparative Example II |
|---|---|---|---|
| Description | Clear, colorless solution, free from any visible particles | Clear, colorless solution, free from any visible particles | Clear, colorless solution, free from any visible particles |
| pH | 7.59 | 7.57 | 7.56 |
| S-Oxide Diastereomer-1 Impurity (%) | 0.21 | 0.09 | 0.12 |
| S-Oxide Diastereomer-2 Impurity (%) | 0.23 | 0.14 | 0.17 |
| Impurity at ~1.12 RRT (%) | — | 0.14 | 0.10 |
| Mono Chloro impurity (%) | 0.11 | 0.06 | 0.07 |
| Highest Unknown Impurity (%) | 0.41 | 0.08 | 0.32 |
| Total Impurities (excluding Monohydroxyl Sugammadex) (%) | 1.81 | 0.50 | 0.98 |
| Monohydroxyl impurity (%) | 1.88 | 0.07 | 0.08 |

Example IV: Stability of Sterile Pharmaceutical Composition

First, 102 pre-filled syringe units prepared according to Example I were measured for pH and assay of sugammadex. Assay of sugammadex in the drug solution was measured using HPLC technique as described in Example VIII. S-oxide diastereomer-1 impurity, s-oxide diastereomer-2 impurity, impurity at ~1.12 RRT, mono chloro impurity, unknown impurities, and mono hydroxyl impurity concentrations were also measured using HPLC technique as described in Example VII.

Then, 90 pre-filled syringe units were subjected to either long term storage conditions or accelerated storage conditions. Long term and accelerated storage conditions were as shown in Table 3 below.

TABLE 3

|  | Storage Condition |
|---|---|
| Long term | 25° C./60% RH |
| Accelerated | 40° C./75% RH |

After one month of storage in either long term storage conditions or accelerated storage conditions, the pre-filled syringe units were measured for pH and also for assay of sugammadex using HPLC technique as described in Example VIII. S-oxide diastereomer-1 impurity, s-oxide diastereomer-2 impurity, impurity at ~1.12 RRT, mono chloro impurity, unknown impurities, and mono hydroxyl impurity concentrations were also measured using HPLC technique as described in Example VII. The same measurements were then repeated after three months of storage in either long term storage conditions or accelerated storage conditions. The results of this study are shown in Table 4.

TABLE 4

| Condition | Initial | 1 Month 25° C./ 60% RH | 3 Month 25° C./ 60% RH | 1 Month 40° C./ 75% RH | 3 Month 40° C./ 75% RH |
|---|---|---|---|---|---|
| | | Test | | | |
| Description | Clear colorless solution free from any visible particles | Clear, colorless solution, free from any visible particles | Clear, colorless solution, free from any visible particles | Clear, colorless solution, free from any visible particles | Clear, colorless solution, free from any visible particles |
| pH | 7.57 | 7.58 | 7.51 | 7.56 | 7.49 |
| Assay | 104.5 | 102.3 | 103.6 | 101.6 | 103.5 |
| | Degradation products | | | | |
| s-oxide diastereomer-1 | 0.08 | 0.09 | 0.09 | 0.10 | 0.17 |
| s-oxide diastereomer-2 | 0.13 | 0.13 | 0.14 | 0.15 | 0.22 |
| Monohydroxy IMP | 0.08 | 0.07 | 0.07 | 0.07 | 0.07 |
| Monochloro IMP | 0.06 | 0.01 | 0.01 | 0.01 | 0.01 |
| Unknown Single Max | 0.08 (RRT 0.93) | 0.10 (RRT-1.12) | 0.11 (RRT 1.12) | 0.10 (RRT-1.12) | 0.10 (RRT 1.12) |
| Total impurities (Excluding monohydroxy) | 0.43 | 0.60 | 0.64 | 0.64 | 0.76 |

Based on the results of this study, it was determined that the sterile pharmaceutical composition pre-filled syringe units prepared according to Example I were stable under both accelerated and long term conditions at least for at least three months.

Example V: Thermal-Forced Degradation of Sugammadex Sodium

To confirm that the impurities observed in Example III were at least in part a result of thermal degradation, sugammadex sodium as a solution in WFI was subjected to an elevated temperature of 60° C. for ten days. S-oxide diastereomer-1 impurity, s-oxide diastereomer-2 impurity, impurity at ~1.12 RRT, mono chloro impurity, unknown impurities, and mono hydroxyl impurity concentrations were measured using HPLC technique as described in Example VII after the first, third, fifth, and tenth day. The results of this study are shown in Table 5 below.

TABLE 5

| Impurity | API Specification (% impurity) | After first day (% impurity) | After third day (% impurity) | After fifth day (% impurity) | After tenth day (% impurity) |
|---|---|---|---|---|---|
| S-oxide diastereomer-1 impurity | NMT 0.09 | 0.12 | 0.14 | 0.16 | 0.48 |
| S-oxide diastereomer-2 impurity | NMT 0.09 | 0.17 | 0.20 | 0.21 | 0.42 |
| Impurity at ~1.12 RRT | NMT 0.09 | 0.10 | 0.10 | 0.10 | 0.08 |
| Mono chloro impurity | NMT 0.09 | 0.04 | 0.03 | 0.03 | 0.03 |
| Highest Unknown impurity | NMT 0.09 | 4.44 | 5.34 | 7.18 | 15.04 |

TABLE 5-continued

| Impurity | API Specification (% impurity) | After first day (% impurity) | After third day (% impurity) | After fifth day (% impurity) | After tenth day (% impurity) |
|---|---|---|---|---|---|
| Other total impurities | — | 0.71 | 0.79 | 0.80 | 0.85 |
| Total impurities | NMT 0.50 | 5.58 | 6.59 | 8.48 | 16.91 |
| (Excluding Monohydroxy impurity) | NMT 7.0 | 0.03 | 0.03 | 0.03 | 0.02 |

Based on the results of this study, it was determined that at least s-oxide diastereomer-1 impurity, s-oxide diastereomer-2 impurity, and unknown impurities are generated via thermal degradation of sugammadex sodium.

Example VI: Oxidative-Forced Degradation of Sugammadex Sodium

To confirm that impurities observed in sugammadex sodium-containing solutions could be at least in part a result of oxidative degradation, sugammadex sodium as a solution in $H_2O_2$ was subjected to an atmosphere of either 0.01% $H_2O_2$ for one hour or to an atmosphere of 0.002% $H_2O_2$ for five hours. S-oxide diastereomer-1 impurity, s-oxide diastereomer-2 impurity, impurity at ~1.12 RRT, mono chloro impurity, unknown impurities, and mono hydroxyl impurity concentrations were measured using HPLC technique as described in Example VII after the first hour of 0.01% $H_2O_2$ exposure and after the first, fourth, and fifth hour of 0.002% $H_2O_2$ exposure. The results of this study are shown in Table 6 below.

TABLE 6

| | API Specification (% impurity) | 0.01% $H_2O_2$ After first hour (% impurity) | 0.002% $H_2O_2$ After first hour (% impurity) | 0.002% $H_2O_2$ After fourth hour (% impurity) | 0.002% $H_2O_2$ After fifth hour (% impurity) |
|---|---|---|---|---|---|
| S-oxide diastereomer-1 impurity | NMT 0.09 | 10.64 | 1.20 | 3.42 | 4.11 |
| S-oxide diastereomer-2 impurity | NMT 0.09 | 12.89 | 1.47 | 4.18 | 5.02 |
| Impurity at ~1.12 RRT | NMT 0.09 | 0.08 | 0.10 | 0.09 | 0.09 |
| Mono chloro impurity | NMT 0.09 | 0.03 | 0.04 | 0.03 | 0.03 |
| Highest Unknown impurity | NMT 0.09 | 3.07 | 0.07 | 0.07 | 0.07 |
| Other total impurities | — | 3.66 | 0.31 | 0.65 | 0.82 |
| Total impurities | NMT 0.50 | 30.36 | 3.20 | 8.45 | 10.14 |
| (Excluding Monohydroxy impurity) | NMT 7.0 | 0.02 | 0.03 | 0.02 | 0.03 |

Based on the results of this study, it was determined that at least s-oxide diastereomer-1 impurity, s-oxide diastereomer-2 impurity, and unknown impurities are generated via oxidation of sugammadex sodium.

Example VII: HPLC Technique—Related Substances

For the following procedure, amber-colored glassware was used for all preparations. In addition, because sugammadex sodium is markedly hygroscopic when exposed to air at room temperature and when exposed to humidity, a relative humidity of less than 40% RH was maintained during weighing.

First, a buffer solution having a pH of 2.0 was prepared by weighing and transferring about 4.08 g of potassium dihydrogen phosphate (AR grade of equivalent) into 1000 mL water (HPLC Grade or Milli-Q) and mixing. The pH of the buffer solution was adjusted to 2.0±0.05 with concentrated ortho-phosphoric acid (HPLC grade or equivalent) and mixed well.

A mobile phase A was then prepared by transferring 950 mL of the buffer solution and 50 mL of methanol (HPLC grade or equivalent) into a bottle, mixing, and sonicating to degas. A mobile phase B was also prepared by transferring 300 mL of the buffer solution and 700 mL of acetonitrile (HPLC grade or equivalent) into a bottle, mixing, and sonicating to degas.

A standard solution (50 ppm) was also prepared by weighing and transferring 27.2 mg of sugammadex sodium standard into a 50 mL amber color volumetric flask. About 30 mL of 100% water (HPLC Grade or Milli-Q) was added, and the mixture was sonicated to dissolve. The solution was made up to the mark with 100% water (HPLC Grade or Milli-Q) and mixed well. Then, 5.0 mL of this solution was transferred to 50 mL amber color volumetric flasks, made up to the mark with 100% water (HPLC Grade or Milli-Q), and mixed well.

To prepare a sensitivity solution (5 ppm), 5.0 mL of the standard solution was transferred to a 50 mL amber volumetric flask, made-up to the mark with 100% water (HPLC Grade or Milli-Q), and mixed well.

A placebo solution was also prepared by weighing and transferring 1.0 g of placebo into a 20 mL amber color volumetric flask, diluting to 20 mL with 100% water (HPLC Grade or Milli-Q), and mixing well.

A sample solution (5000 ppm) was also prepared by weighing and transferring 1.0 g of the sample to be analyzed into a 20 mL amber color volumetric flask, diluting to 20 mL with 100% water (HPLC Grade or Milli-Q), and mixing well.

Next, a liquid chromatography system was set up with the parameters shown in Table 7.

TABLE 7

| | | |
|---|---|---|
| Mobile Phase | Mobile Phase A Mobile Phase B | |
| Column | Primesil C18, 250 × 4.6 mm, 3μ | |
| Column Temperature | 50° C. | |
| Sample Temperature | 5° C. | |
| Flow Rate | 0.8 mL/min | |
| Wavelength | 210 nm | |
| Injection Volume | 10 μL | |
| Retention time | About 30 min | |

| | Time (In min) | Mobile Phase A (%) | Mobile Phase B (%) |
|---|---|---|---|
| Gradient for Standard solution | 0 | 80 | 20 |
| | 5 | 78 | 22 |
| | 35 | 75 | 25 |
| | 36 | 80 | 20 |

TABLE 7-continued

| | 45 | 80 | 20 |
|---|---|---|---|
| | Time (In min) | Mobile Phase A (%) | Mobile Phase B (%) |
| Gradient for Blank, Sample and Placebo | 0 | 80 | 20 |
| | 5 | 78 | 22 |
| | 35 | 75 | 25 |
| | 38 | 70 | 30 |
| | 45 | 70 | 30 |
| | 60 | 45 | 55 |
| | 65 | 80 | 20 |
| | 70 | 80 | 20 |
| Needle wash | Water:Acetonitrile (10:90) v/v | | |
| Seal wash | Water:Acetonitrile (90:10) v//v | | |
| System Suitability | 1. S/N ratio of Sensitivity solution not less than 10. 2. The RSD of sugammadex area should NMT 5.0% from six replicate injection of standard solution. 3. Theoretical Plate Count of sugammadex peak in first injection from six replicate injections and last Bracketing standard injection should not be less than 2000. 4. The USP Tailing factor of sugammadex peak in first injection from six replicate injections and last Bracketing standard injection should not be more than 2.0. 5. The RSD of sugammadex area should NMT 5.0% from Bracketing injection of standard solution. | | |

The chromatographic procedure was then performed using the injection sequence shown in Table 8.

TABLE 8

| Sample Name | No. of Injection |
|---|---|
| Diluent as a Blank | 1 |
| Sensitivity Solution | 1 |
| Standard Solution | 6 |
| Diluent as a Blank | 1 |
| Placebo Preparation | 1 |
| Sample Preparation *-1 | 1 |
| Sample Preparation *-2 | 1 |
| Diluent as a Blank | 1 |
| Standard Solution (Bracketing) | 1 |

When performing the chromatographic procedure, for initial samples, two samples were prepared in duplicate. For stability samples, a single sample was prepared. In addition, any peak due to blank and/or placebo was disregarded, any peak below LOQ level was disregarded, and any peak corresponding to mono chloro impurity was disregarded.

Using the above procedure, impurities were observed at about the RRTs shown in Table 9.

TABLE 9

| Sr. No | Name of Impurity | RRT |
|---|---|---|
| 1 | s-oxide diastereomer-1 | 0.57 |
| 2 | s-oxide diastereomer-2 | 0.67 |
| 3 | mono hydroxy impurity | 0.75 |
| 4 | mono chloro impurity | 1.46 |
| 5 | sugammadex | 1.00 |

The percent impurity was then calculated as follows:

$$\text{Known impurity}(\%) = \frac{A(Spl)}{A(Std)} \times \frac{Wt(Std)}{50} \times \frac{5}{50} \times \frac{20}{Wt(Spl)} \times \frac{D}{LC} \times \frac{(P-WC)}{100} \times \frac{2002.12}{2178.01} \times 100$$

where:

A(Spl)=Peak response of impurity obtained from sample solution

A(Std)=Average peak response of sugammadex from the standard solution

Wt(Std)=Weight (mg) of sugammadex working standard.

Wt(Spl)=Weight (g) of Sample

LC=Label Claim (100 mg/ml sugammadex)

D=Density of sample (mg/ml)

P=Potency of the standard (Anhydrous basis+Solvent free)

WC=Water content of sugammadex working standard.

2002.12=Molecular weight of sugammadex 2178.01=Molecular weight of sugammadex sodium Total impurities were calculated by adding all known impurities (excluding mono hydroxy impurity) and all unknown impurities.

Example VIII: HPLC Technique—Assay

For the following procedure, amber-colored glassware was used for all preparations. In addition, because sugammadex sodium is markedly hygroscopic when exposed to air at room temperature and when exposed to humidity, a relative humidity of less than 40% RH was maintained during weighing.

First, a buffer solution having a pH of 2.0 was prepared by weighing and transferring about 4.08 g of potassium dihydrogen phosphate (AR grade or equivalent) into 1000 mL water (HPLC Grade or Milli-Q) and mixing. The pH of the buffer solution was adjusted to 2.0±0.05 with concentrated ortho-phosphoric acid (HPLC grade or equivalent), mixed well, and filtered through a 0.45 μm membrane filter.

A mobile phase was then prepared by transferring 830 mL of the buffer solution and 170 mL of acetonitrile (HPLC grade or equivalent) into a bottle and mixing. A diluent was also prepared by degassing a mixture of 830 mL of the buffer solution and mixing with 170 mL of acetonitrile (HPLC grade or equivalent).

A standard solution (800 ppm) was also prepared by weighing and transferring 87 mg of sugammadex sodium standard into a 100 mL amber-colored volumetric flask. About 60 mL of the diluent was added, and the mixture was sonicated to dissolve. The solution was made up to the mark with the diluent and mixed well.

A sample solution (800 ppm) was also prepared by weighing and transferring 4.0 g of sample into a 50 mL amber-colored volumetric flask, diluting to volume with the diluent, and mixing well. Then, 5 mL of the resulting solution was diluted to 50 mL with diluent. (It was determined that the standard weight and sample volume can be changed as far as to meet the final concentration.)

Next, a liquid chromatography system was set up with the parameters shown in Table 10.

TABLE 10

| | |
|---|---|
| Mobile Phase | Buffer:Acetonitrile (83:17) v/v |
| Column | X bridge C18, (50 × 4.6) mm 3.5μ |
| Column Temperature | 50° C. |
| Sample Temperature | 5° C. |
| Flow Rate | 1.2 mL/min |
| Wavelength | 210 nm |
| Injection Volume | 10 μL |
| Run Time | 7 min |
| Needle wash | Water:Acetonitrile (10:90) v/v |
| Seal wash | Water:Acetonitrile (90:10) v//v |
| System Suitability | 1. The RSD of sugammadex area should NMT 2.0% from five replicate injection of standard solution.<br>2. Theoretical Plate Count of sugammadex peak in first injection from five replicate injections and last Bracketing standard injection should not be less than 2000.<br>3. The USP Tailing factor of sugammadex peak in first injection from five replicate injections and last Bracketing standard injection should not be more than 2.0.<br>4. The RSD of sugammadex area should NMT 2.0% from Bracketing injection of standard solution.<br>5. The % deviation between standard and check standard should be not more than ±2.0% |

The chromatographic procedure was then performed using the injection sequence shown in Table 11.

TABLE 11

| Sample Name | No. of Injection |
|---|---|
| Blank | 1 |
| Standard Solution | 5 |
| Check Standard Solution | 2 |
| Blank | 1 |
| Sample Preparation Set-1 | 1 |
| Sample Preparation Set-2* | 1 |
| Standard Solution (Bracketing) | 1 |

The sample preparation in set-1 was applicable for stability and set-2 for initial analysis. The percent deviation was calculated using the following formula:

$$\% \text{ deviation} = \frac{(\text{Avg. standard response/standard weight}) - (\text{Avg. check standard response/check standard weight})}{(\text{Avg. standard response/standard weight})} \times 100$$

Then, the assay of sugammadex (mg/mL) was determined using the following formula, where Y is assay of sugammadex (mg/mL):

$$Y = \frac{A(Spl)}{A(Std)} \times \frac{Wt(Std)}{100} \times \frac{50}{Wt(Spl)} \times \frac{50}{5} \times \frac{D}{1} \times \frac{(P-WC)}{100} \times \frac{2002.12}{2178.01} \times 100$$

where:
A(Spl)=Peak response of sugammadex obtained from sample solution
A(Std)=Average peak response of sugammadex from the standard solution
Wt(Std)=Weight (mg) of sugammadex working standard.
Wt(Spl)=Weight in g of Sample
D=Density of sample in g/ml
P=Potency of the standard (Anhydrous basis+solvent free basis)
WC=Water content of sugammadex working standard.
2002.12=Molecular weight of sugammadex
2178.01=Molecular weight of sugammadex sodium The assay of sugammadex was then calculated using the following formula:

$$Assay(\%LC) = \frac{Y}{LC} \times 100$$

where LC is the label claim 100 mg/mL of sugammadex.
The assay of sugammadex was then reported as follows:

Assay % (sugammadex+mono hydoxy sugammadex)
=% Assay of sugammadex+% of mono hydroxy sugammadex content obtained from related compounds.

What is claimed is:

1. A sterile pharmaceutical product provided in a pre-filled syringe, wherein the sterile pharmaceutical product is prepared by a method comprising:
   solubilizing an active agent and a pH adjusting agent in a solvent to provide a pharmaceutical composition,
   filtering the pharmaceutical composition through a membrane to provide a sterile pharmaceutical composition, and
   providing the sterile pharmaceutical composition in a pre-filled syringe having a labeled size, wherein:
   the active agent comprises sugammadex,
   the pre-filled syringe has a headspace volume that is less than 7.5% of the labeled size, and
   the method is free of a heat-based sterilization process.

2. The sterile pharmaceutical product of claim 1, wherein the active agent is sugammadex sodium.

3. The sterile pharmaceutical product of claim 1, wherein the pH adjusting agent comprises hydrochloric acid, sodium hydroxide, or a combination thereof, and wherein the solvent comprises WFI.

4. The sterile pharmaceutical product of claim 1, wherein the heat-based sterilization process comprises subjecting the pharmaceutical composition to a temperature of 120° C. or greater.

5. The sterile pharmaceutical product of claim 1, wherein the sterile pharmaceutical composition has an initial total impurity concentration of no more than about 1.0% (w/w).

6. The sterile pharmaceutical product of claim 1, wherein the sterile pharmaceutical composition has a total impurity concentration of no more than about 1.0% (w/w) after one month of storage in long term storage conditions.

7. The sterile pharmaceutical product of claim 1, wherein the membrane has an average pore size of about 0.2 μm.

8. The sterile pharmaceutical product according to claim 1, wherein the sterile pharmaceutical product has a shelf life of at least three months.

* * * * *